(12) United States Patent
Ogino et al.

(10) Patent No.: US 11,819,351 B2
(45) Date of Patent: Nov. 21, 2023

(54) MEDICAL IMAGING APPARATUS, MEDICAL IMAGE PROCESSING APPARATUS, AND IMAGE PROCESSING PROGRAM

(71) Applicant: Hitachi, Ltd., Tokyo (JP)

(72) Inventors: Masahiro Ogino, Tokyo (JP); Zisheng Li, Tokyo (JP); Yukio Kaneko, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 396 days.

(21) Appl. No.: 17/134,843

(22) Filed: Dec. 28, 2020

(65) Prior Publication Data

US 2021/0272277 A1 Sep. 2, 2021

(30) Foreign Application Priority Data

Feb. 28, 2020 (JP) ................................. 2020-033780

(51) Int. Cl.
*A61B 6/00* (2006.01)
*G06T 7/00* (2017.01)
(Continued)

(52) U.S. Cl.
CPC ............ *A61B 6/5217* (2013.01); *A61B 5/055* (2013.01); *A61B 5/7267* (2013.01);
(Continued)

(58) Field of Classification Search
CPC ... A61B 6/5217; A61B 8/5223; G06T 7/0012; G06N 20/00
See application file for complete search history.

(56) References Cited

U.S. PATENT DOCUMENTS 8,194,959 B2 * 6/2012 Sakaida ............... G06V 10/457
382/128
10,140,544 B1 * 11/2018 Zhao ..................... G06N 20/00
(Continued)

FOREIGN PATENT DOCUMENTS

JP 2002-253539 A 9/2002

OTHER PUBLICATIONS

Singanamalli A., et al., "Identifying in vivo DCE MRI Markers Associated with Microvessel Architecture and Gleason Grades of Prostate Cancer", Journal of Magnetic Resonance, Jan. 2016, pp. 149-158, vol. 43, Issue No. 1 (19 pages).
(Continued)

*Primary Examiner* — John Villecco
*Assistant Examiner* — Courtney Joan Nelson
(74) *Attorney, Agent, or Firm* — Crowell & Moring LLP

(57) ABSTRACT

To obtain a predictive model that shows a diagnostic prediction result with higher accuracy and high medical validity. A medical imaging apparatus includes an imaging unit that collects an image signal of an inspection target, and an image processing unit that generates first image data from the image signal and performs image processing of the first image data. The image processing unit includes a feature quantity extraction unit that extracts a first feature quantity from the first image data, a feature quantity abstraction unit that abstracts the first feature quantity to extract a second feature quantity, a feature quantity conversion unit that converts the second feature quantity into a third feature quantity extracted by second image data, and an identification unit that uses the converted third feature quantity to calculate a predetermined parameter value.

14 Claims, 25 Drawing Sheets

(51) Int. Cl.
| | |
|---|---|
| *G16H 30/20* | (2018.01) |
| *G06N 20/00* | (2019.01) |
| *G06N 5/02* | (2023.01) |
| *A61B 5/055* | (2006.01) |
| *A61B 5/00* | (2006.01) |
| *A61B 6/03* | (2006.01) |
| *A61B 8/00* | (2006.01) |
| *A61B 8/08* | (2006.01) |
| *G06F 18/21* | (2023.01) |
| *G06V 10/82* | (2022.01) |
| *G06V 10/44* | (2022.01) |

(52) U.S. Cl.
CPC .......... *A61B 5/7275* (2013.01); *A61B 5/7485* (2013.01); *A61B 6/032* (2013.01); *A61B 6/469* (2013.01); *A61B 8/469* (2013.01); *A61B 8/5223* (2013.01); *G06F 18/217* (2023.01); *G06N 5/02* (2013.01); *G06N 20/00* (2019.01); *G06T 7/0012* (2013.01); *G06V 10/82* (2022.01); *G16H 30/20* (2018.01); *G06T 2207/10081* (2013.01); *G06T 2207/10088* (2013.01); *G06T 2207/10132* (2013.01); *G06T 2207/20081* (2013.01); *G06V 10/454* (2022.01); *G06V 2201/03* (2022.01)

(56) References Cited

U.S. PATENT DOCUMENTS

| | | | |
|---|---|---|---|
| 2014/0375671 | A1 | 12/2014 | Giger et al. |
| 2017/0330320 | A1* | 11/2017 | Lynch .................... G16H 50/20 |
| 2018/0108125 | A1* | 4/2018 | Beymer ................. G06V 40/10 |
| 2018/0144214 | A1* | 5/2018 | Hsieh .................... G06T 7/0002 |
| 2019/0304092 | A1* | 10/2019 | Akselrod-Ballin .... G06N 3/084 |

OTHER PUBLICATIONS

Burnside E., et al., "Using Computer Extracted Image Phenotypes from Tumors on Breast Magnetic Resonance Imaging to Predict Breast Cancer Pathologic Stage.", Cancer, Mar. 2016, pp. 748-757, vol. 122, Issue No. 5 (24 pages).

Japanese-language Office Action issued in Japanese Application No. 2020-033780 dated Dec. 27, 2022 with English translation (10 pages).

* cited by examiner

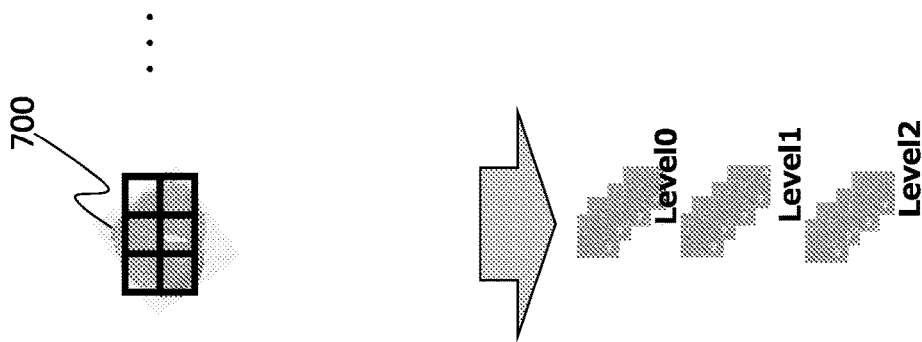
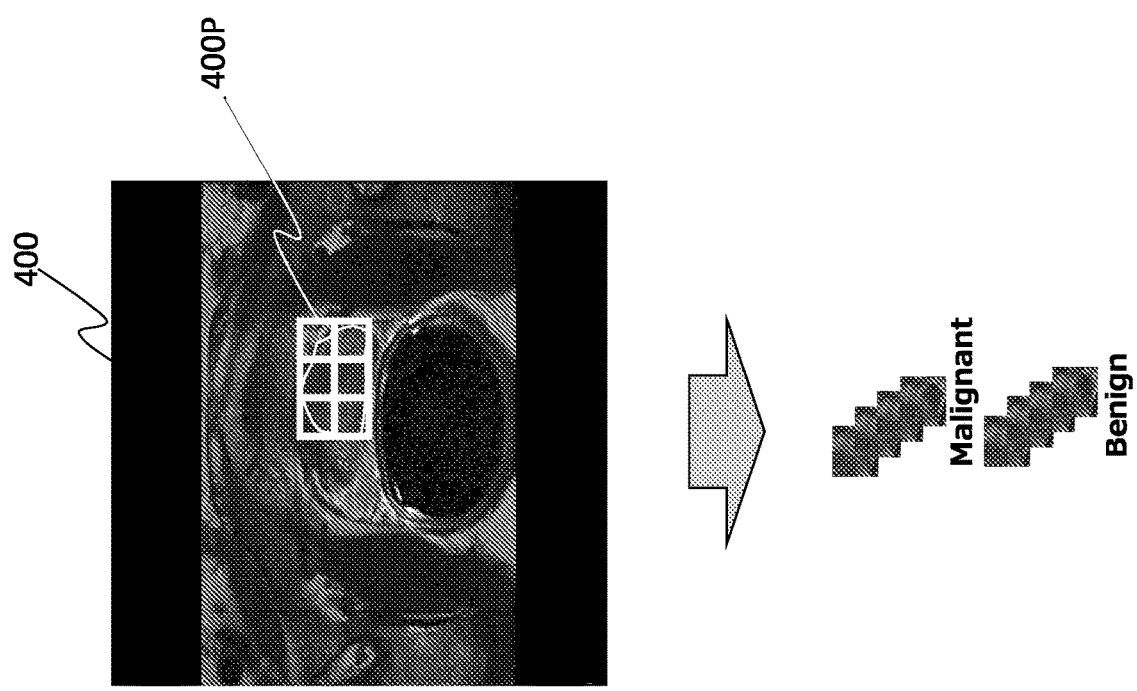

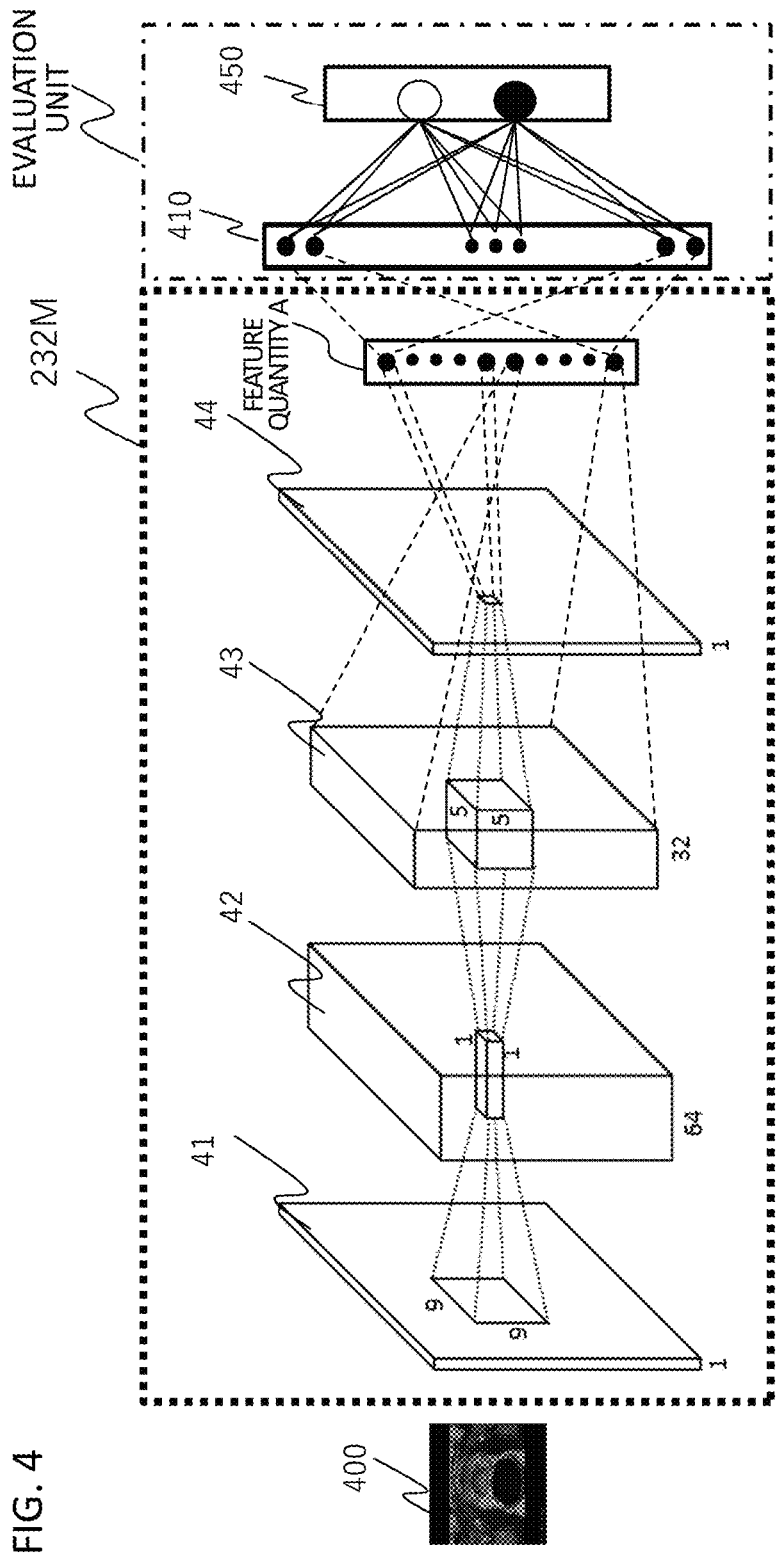

MEDICAL IMAGING APPARATUS, MEDICAL IMAGE PROCESSING APPARATUS, AND IMAGE PROCESSING PROGRAM

INCORPORATION BY REFERENCE

The present application claims priority from Japanese patent application JP2020-033780 filed on Feb. 28, 2020, the content of which is hereby incorporated by reference into this application.

BACKGROUND OF THE INVENTION

Field of the Invention

The present invention relates to an image processing technology for processing a medical image acquired by a medical imaging apparatus such as a magnetic resonance imaging (hereinafter referred to as MRI) apparatus, a CT apparatus, or an ultrasonic imaging apparatus, and particularly relates to an image diagnosis support technology for advanced diagnosis using a medical image and prediction of a treatment policy.

Description of the Related Art

In recent years, as an image diagnosis support technology to which artificial intelligence (AI) is applied, a method using deep learning (DL) to predict the presence or absence of a disease (for example, a tumor) and a malignancy (grade) has been proposed. In this method, a convolutional neural network (CNN) trained to classify an image into a plurality of categories is generally used.

As an example of a method of predicting a grade of tumor malignancy using DL, Asha Singanamalli et al., "Identifying in vivo DCE MRI markers associated with microvessel architecture and gleason grades of prostate cancer.", Journal of Magnetic Resonance, 2015, 43, p. 149-158 discloses a predictive model in which a plurality of image feature quantities is obtained from each of image data and pathological image data captured by dynamic contrast MRI (DCE-MRI), a map obtained by combining the respective feature quantities is generated, and a relationship between the feature quantity and the Gleason score (GS) information used for stage calculation of prostate cancer is analyzed from this map, thereby estimating GS for a new input image.

In addition, US 2014/0,375,671 discloses a method of extracting a plurality of image feature quantities of an MRI image and presenting a map image arranged for each feature quantity. This map image is generated by analyzing a relationship between a plurality of feature quantities and a plurality of pathological conditions (malignancy, etc.), and it is possible to correlate information about the pathological condition from the MRI image of the subject.

However, in order to obtain a diagnosis result using the technology of Asha Singanamalli et al., "Identifying in vivo DCE MRI markers associated with microvessel architecture and gleason grades of prostate cancer.", Journal of Magnetic Resonance, 2015, 43, p. 149-158, in addition to an examination by the medical imaging apparatus, a pathological examination for obtaining a pathological image of an examination site is necessary. Since a micro tissue of a patient is collected using a needle, etc. in a pathological examination, a physical burden on the patient is large, and it is desired to have a technology capable of determining the presence or absence of a tumor and a grade of malignancy without performing a pathological examination. From another point of view, it is possible to provide optimal medical care by having a technology capable of accurately determining a target that needs to be subjected to a pathological examination.

In addition, in the case of using the technology of US 2014/0,375,671, the relationship between the image feature quantity and the pathological condition is derived from analysis of a large amount of data, and it is difficult to indicate validity from a medical viewpoint. In other words, in the case of use in an actual medical field, there is a high possibility that a black box of processing content becomes a problem.

As a method of predicting and presenting a nature of a tumor that can be determined by a pathological examination from an image of a medical imaging apparatus without performing a pathological diagnosis, Elizabeth S. Burnside et al., "Using computer extracted image phenotypes from tumors on breast magnetic resonance imaging to predict breast cancer pathologic stage.", Cancer, 2016, p. 748-757 discloses a method of predicting a pathological image finding from an input of a medical imaging apparatus image by learning a lot of combinations (pair data) of medical imaging apparatus images and pathological diagnosis results (findings, text information).

In the method disclosed in Elizabeth S. Burnside et al., "Using computer extracted image phenotypes from tumors on breast magnetic resonance imaging to predict breast cancer pathologic stage.", Cancer, 2016, p. 748-757, it is possible to predict and present findings (tumor malignancy, grade, etc.) obtained from pathological examinations using medical images without conducting pathological examinations.

However, this method is a method for deriving a relationship among the medical imaging apparatus image, the image of pathological findings and text from the analysis of a large amount of data, and description is difficult from a viewpoint of validity from a medical point of view similarly to the method of US 2014/0,375,671. In addition, in this method, since a learning model is created using a combination of different information levels of a medical imaging apparatus image and a pathological finding (text) as a learning sample, a correlation becomes a black box, and infallibility of a prediction result may not be verified.

SUMMARY OF THE INVENTION

An object of the invention is to use DL to obtain a predictive model that shows a diagnostic prediction result with higher accuracy and high medical validity.

To solve the above-mentioned problem, the invention performs a process in which after an image signal of an image acquired by an imaging unit is converted into image data to extract a first feature quantity from the image data, the first feature quantity is abstracted to obtain a second feature quantity, the second feature quantity is converted into a third feature quantity extracted from an image having detailed diagnostic information, and a prediction result is obtained using the third feature quantity.

Specifically, a medical imaging apparatus includes an imaging unit that collects an image signal of an inspection target, and an image processing unit that generates first image data from the image signal and performs image processing of the first image data. The image processing unit includes a feature quantity extraction unit that extracts a first feature quantity from the first image data, a feature quantity abstraction unit that extracts (abstracts) a more important second feature quantity from the first feature quantity, a feature quantity conversion unit that converts the second feature quantity into a third feature quantity extracted by second image data different from the first image data, and an identification unit that uses the converted third feature quantity to calculate a predetermined parameter value, and performs prediction.

According to the invention, it is possible to obtain more accurate diagnostic information by extracting a feature and abstracting the extracted feature using image data generated from an image signal collected by an imaging unit, and converting between an abstracted feature and a feature of an image having highly accurate diagnostic information. In this way, it is possible to realize diagnosis using a medical imaging apparatus with higher accuracy, which can contribute to improvement in medical quality. In addition, medical validity can be ensured by providing an understandable process in processing, rather than merely inputting an image and processing the image in a black box to obtain diagnostic information.

BRIEF DESCRIPTION OF THE DRAWINGS

FIGS. 3A and 3B are diagrams for description of patch processing of an input image and a pathological image, respectively;

FIG. 4 is a diagram illustrating an example of a structure of a feature quantity extraction unit (CNN);

DETAILED DESCRIPTION OF THE INVENTION

The invention can be applied to various medical imaging apparatuses including an imaging unit that acquires a medical image and an image processing unit, such as an MRI apparatus, a CT apparatus, and an ultrasonic imaging apparatus. First, embodiments having configurations common to each modality will be described.

First Embodiment

Figure 1:
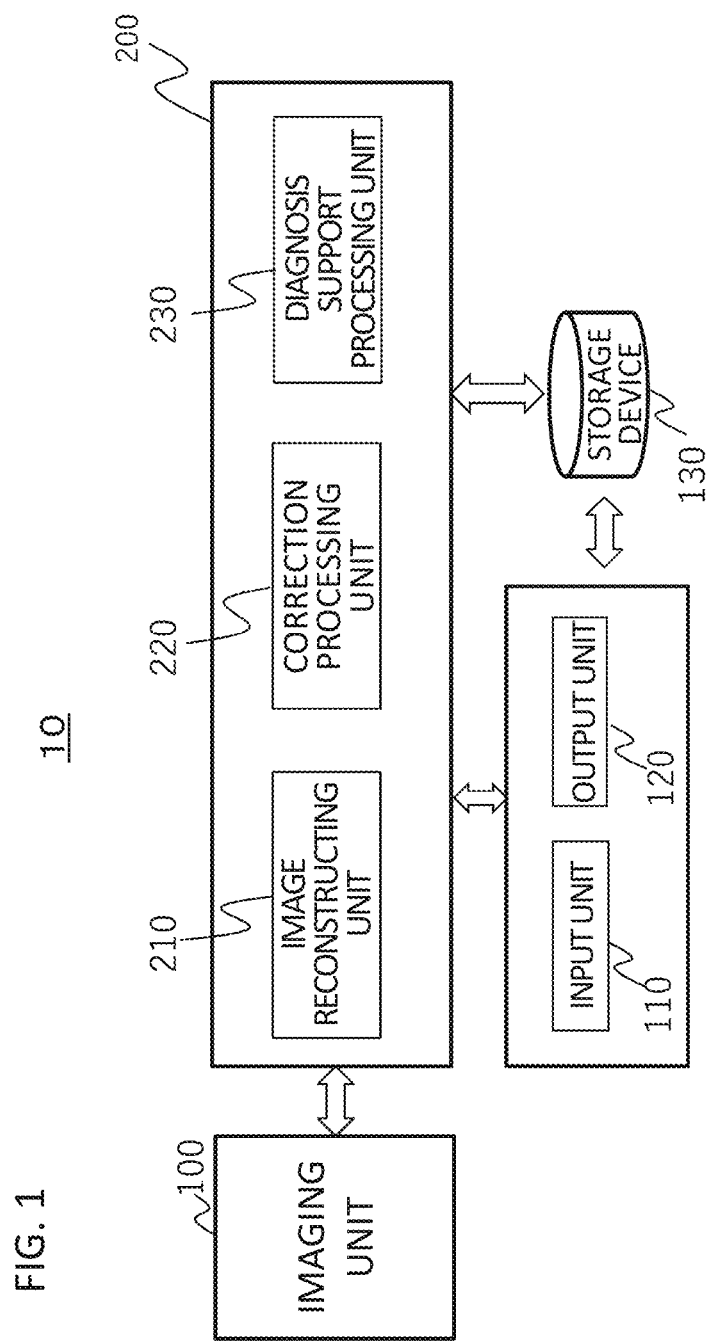
FIG. 1 is a diagram illustrating an overall configuration of a medical imaging apparatus according to a first embodiment.

As illustrated in FIG. 1, a medical imaging apparatus 10 according to the present embodiment includes an imaging unit 100 that collects an image signal necessary for image reconstruction from a subject and an image processing unit 200 that performs image processing of the subject imaged by the imaging unit 100. The medical imaging apparatus 10 further includes an input unit 110 for inputting various instructions, an output unit 120 such as a display, and a storage device 130 on the inside or outside thereof.

The imaging unit 100, which has a different configuration depending on the modality, acquires an image signal by measuring the subject and passes the acquired image signal to the image processing unit 200. The detailed configuration for each modality will be described in an embodiment described later.

The image processing unit 200 includes an image reconstructing unit 210 that reconstructs an image (first image) from the image signal received from the imaging unit 100 and a diagnosis support processing unit 230 that performs a process for supporting image diagnosis using image data created by the image reconstructing unit 210. The image processing unit 200 may further include a correction processing unit 200 that performs a predetermined correction process such as noise processing on the image data (including creating a new image by another inter-image calculation) before inputting the image data created by the image reconstructing unit 210 to the diagnosis support processing unit 230, and FIG. 1 illustrates a case where such a correction processing unit 220 is included. Image data of the image created by the image reconstructing unit 210 or the image corrected by the correction processing unit 220 and image data of the image processed by the diagnosis support processing unit 230 are output to the output unit 120.

Figure 2:
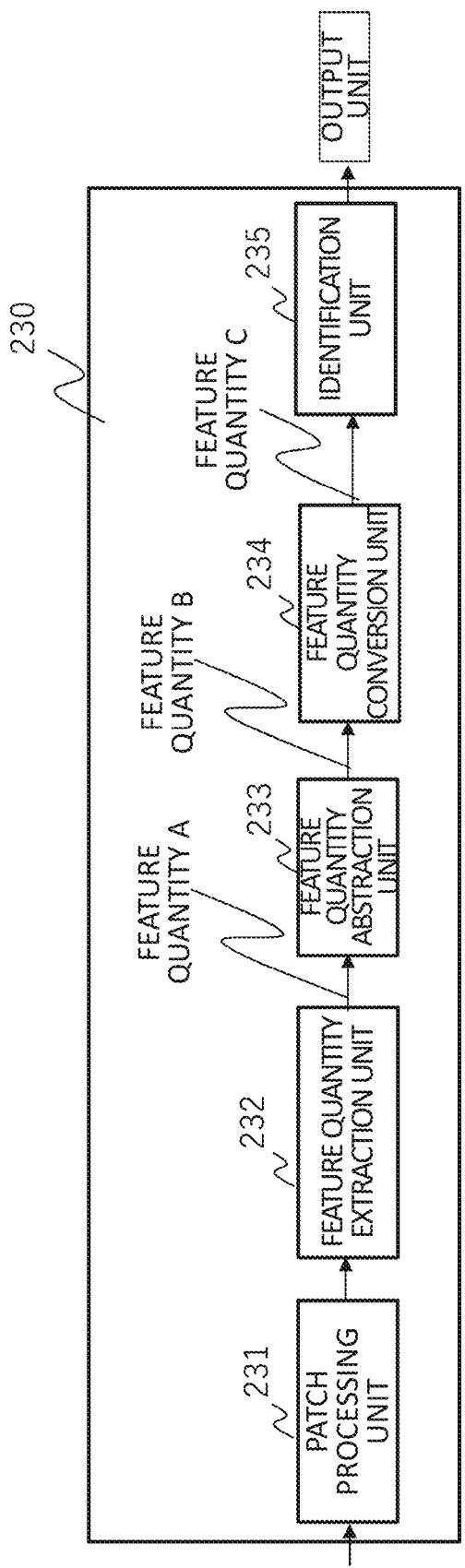
FIG. 2 is a diagram illustrating a configuration of a diagnosis support processing unit according to the first embodiment.

As illustrated in FIG. 2, the diagnosis support processing unit 230 includes a feature quantity extraction unit 232 that extracts a first feature quantity A from first image data received from the correction processing unit 220, a feature quantity abstraction unit 233 that extracts a second feature quantity B from the first feature quantity, a feature quantity conversion unit 234 that converts the second feature quantity B into a third feature quantity C using a feature quantity conversion model, and an identification unit 235 that calculates a predetermined parameter value using the third feature quantity C using an identification model and performs prediction. Each of the feature quantity extraction unit 232, the feature quantity abstraction unit 233, and the feature quantity conversion unit 234 includes a learning model (DL) learned by machine learning. The diagnosis support processing unit 230 may be a combination of independent learning models of the respective units, or may be one DL that fuses the learning models of the respective units.

The feature quantity A which is an output of the feature quantity extraction unit 232 is a feature quantity extracted from image data of an image (hereinafter referred to as an input image) obtained from an image signal acquired by the imaging unit 100, and is, for example, an output result of an intermediate layer in which brightness information of a lesion part is learned by the DL. The feature quantity B output by the feature quantity abstraction unit 233 is a result of learning by integrating the feature quantity A obtained from the brightness information of each lesion part and extracting a particularly important feature quantity component therefrom.

The feature quantity C output from the feature quantity conversion unit 234 is a feature quantity extracted from the image data of the second image different from the medical image (first image) obtained from the medical imaging apparatus. The second image is an image having more detailed information than that of the first image data in order to identify a lesion, and is, for example, a pathological image and an output result of the intermediate layer in which the DL learns information (feature) in the pathological image of the same part as that of the input image. For example, parameters calculated by the identification unit 240 from the feature quantity C are the presence or absence of a tumor diagnosed from a pathological image, a grade thereof, malignancy of a disease, etc.

The diagnosis support processing unit 230 does not normally use the image data without change as an input image of the feature quantity extraction unit 232, and divides the image data into patches of a predetermined size and performs processing for each patch. In such a case, a patch processing unit 231 that cuts out one or more patches from the image data received from the correction processing unit 220 is further included. As illustrated in FIG. 3A, the patch processing unit 231 cuts out a patch 400P from the image data 400 and passes a plurality of cut-out patches to the feature quantity extraction unit 232, the feature quantity extraction unit 232 extracts the feature quantity A for each patch, and the feature quantity abstraction unit 233 extracts the main feature quantity B common to all patches of the learning data. Patch information is integrated here. The feature quantity conversion unit 234 converts the abstracted feature quantity B into the feature quantity C, and the identification unit 235 calculates a parameter value from the feature quantity C and outputs a prediction result to the output unit 120. Note that in the present embodiment, the feature quantity A extracted for each of a plurality of pieces of image data (here, patches) is integrated by the feature quantity abstraction unit 233 to form the feature quantity B. Thus, when the image data 500 is divided into patches, it is unnecessary to perform alignment with a patch (FIG. 3B) cut out when the feature quantity C is extracted from the second image (for example, a pathological image 700).

Data and programs required for processing of the image processing unit 200 are stored in the storage device 130. The data necessary for the processing of the image processing unit 200 is the data used for processing performed by the image reconstructing unit 210, the correction processing unit 220, and the diagnosis support processing unit 230, and as for the diagnosis support processing unit 230, the data and programs are, for example, each learning model, etc. described later, which is used for processing performed by the feature quantity extraction unit 232, the feature quantity abstraction unit 233, the feature quantity conversion unit 234, and the identification unit 235. The storage device 130 may be a server device of a workstation or picture archiving and communication systems (PACS) communicatively connected to the medical imaging apparatus 10 via a network, or may be a portable storage medium connectable to the medical imaging apparatus 10. In addition, instead of the storage device 130, a cloud connected to the imaging unit 100 via a network may be used as a mechanism for storing each piece of data.

When the medical imaging apparatus 10 includes a CPU and a GPU as a calculation unit and a controller, a function of the image processing unit 200 is realized as software installed in the CPU or the GPU. In particular, the feature quantity extraction unit 232, the feature quantity abstraction unit 233, the feature quantity conversion unit 234, and the identification unit 235 are realized by a neural network having a learning function, and a publicly known software package such as the CNN can be used. In addition, some functions of the image processing unit 200 can be realized by hardware such as an application specific integrated circuit (ASIC) and a field programmable gate array (FPGA).

Hereinafter, a description will be given of a specific configuration of the diagnosis support processing unit 230 of the image processing unit 200 of FIG. 1. First, a learning model to be incorporated in the diagnosis support processing unit 230 will be described.

[Structure of Learning Model]

The learning model of the present embodiment has four types of learning models used by the feature quantity extraction unit 232, the feature quantity abstraction unit 233, the feature quantity conversion unit 234, and the identification unit 235, respectively, and a CNN is used for each learning model.

A first model is a predictive model in which the feature quantity extraction unit 232 extracts the feature quantity A from image data of an input image, a second model is a model for the feature quantity abstraction unit 233 to extract the feature quantity B abstracted from the feature quantity A, a third model is a feature quantity conversion model for the feature quantity conversion unit 234 to convert the feature quantity B into the feature quantity C, and a fourth model in which the identification unit 235 calculates a predetermined parameter value from the feature quantity C and performs a prediction. Furthermore, even though a predictive model for separately obtaining the feature quantity C that is the output of the feature quantity conversion unit 234 and a feature quantity extracted from a different image from the input image is required, since this predictive model is the same as the model for extracting the feature quantities A and B, except that the input images are different, a redundant description is omitted. Note that even though each of the feature quantity extraction unit 232, the feature quantity abstraction unit 233, the feature quantity conversion unit 234, and the identification unit 235 uses a learned model (predictive model), a learning process of the learning model may be performed by the diagnosis support processing unit 230, or may be performed by another arithmetic unit (not illustrated) and stored in the storage device 130.

First, a first predictive model will be described. This predictive model 232M is a model learned using a combination of an input image and a label such as the presence or absence (benign or malignant) of a lesion or a grade of lesion malignancy as learning data.

As schematically illustrated in FIG. 4, a CNN 40 of the predictive model 232M is a computing unit constructed on a computer configured to repeat a convolution operation and pooling 43 a plurality of times between an input layer 41 and an output layer 44 on a multi-layer network. In FIG. 4, a number in front of a block indicating each layer is the number of layers, and a number in each layer represents a size processed by each layer. The CNN of this predictive model is learned to extract a feature quantity A 410 for accurately identifying the presence or absence of the lesion of an input image 400 by the CNN repeating the convolution calculation and pooling on input data of the input image 400 for learning divided into a plurality of patches by the patch processing unit 231.

Learning is performed until an error between an output and teacher data falls within a predetermined range. An error function used at this time will be described after the structure of the learning model.

Note that in FIG. 4, a part surrounded by a one-dot chain line is a part (evaluation unit) incorporated for learning so that a feature quantity highly related to a parameter (presence or absence of tumor, grade, malignancy of disease, etc.) 450 which is an output of an identification layer 234 is extracted as the feature quantity A at the time of learning of the CNN 40, and is unnecessary in a process of operating this predictive model. Hereinafter, this description is similarly applied to FIGS. 5, 7, and 8 to be referred to.

The feature quantity A, which is the output of the predictive model 232M, expresses a plurality of classifications necessary for diagnosis of a feature of an image as a vector of a plurality of dimensions (for example, 1,024 dimensions), and a feature related to a parameter (for example, whether a tumor is benign or malignant) is extracted. Such a feature quantity A is obtained for each patch. Note that in FIG. 4, the feature quantity A 410 is an output of a final layer of all the combined layers. However, the invention is not limited thereto. Even though the deeper the layer, the greater the degree of feature abstraction, it is possible to use an output of a layer shallower than the final layer as the feature quantity.

With regard to a configuration of a CNN network, a typical architecture (AlexNet, VGG-16, VGG-19, etc.) may be used, or a model obtained by pre-learning the architecture using an ImageNet database, etc. may be used.

Next, a description will be given of a second model used in the feature quantity abstraction unit 233, which is a predictive model 233M for extracting the feature quantity B abstracted from the feature quantity A.

The predictive model 233M receives a feature quantity corresponding to the number of patches output from the feature quantity extraction unit 232 as an input, and extracts a main feature quantity that contributes to the presence or absence of a lesion (benign or malignant) or a grade of lesion malignancy. For example, when the number of patches is 200 and the feature quantity is 1,024 dimensions, a feature quantity obtained by connecting feature quantities of 1,024 dimensions×200 is input to this model, and a feature quantity B 420 that contributes most to the presence or absence of lesion (benign or malignant) is finally extracted. The dimension of the output feature quantity B is the same as the dimension of one patch (for example, 1,024 dimensions).

Figure 5:
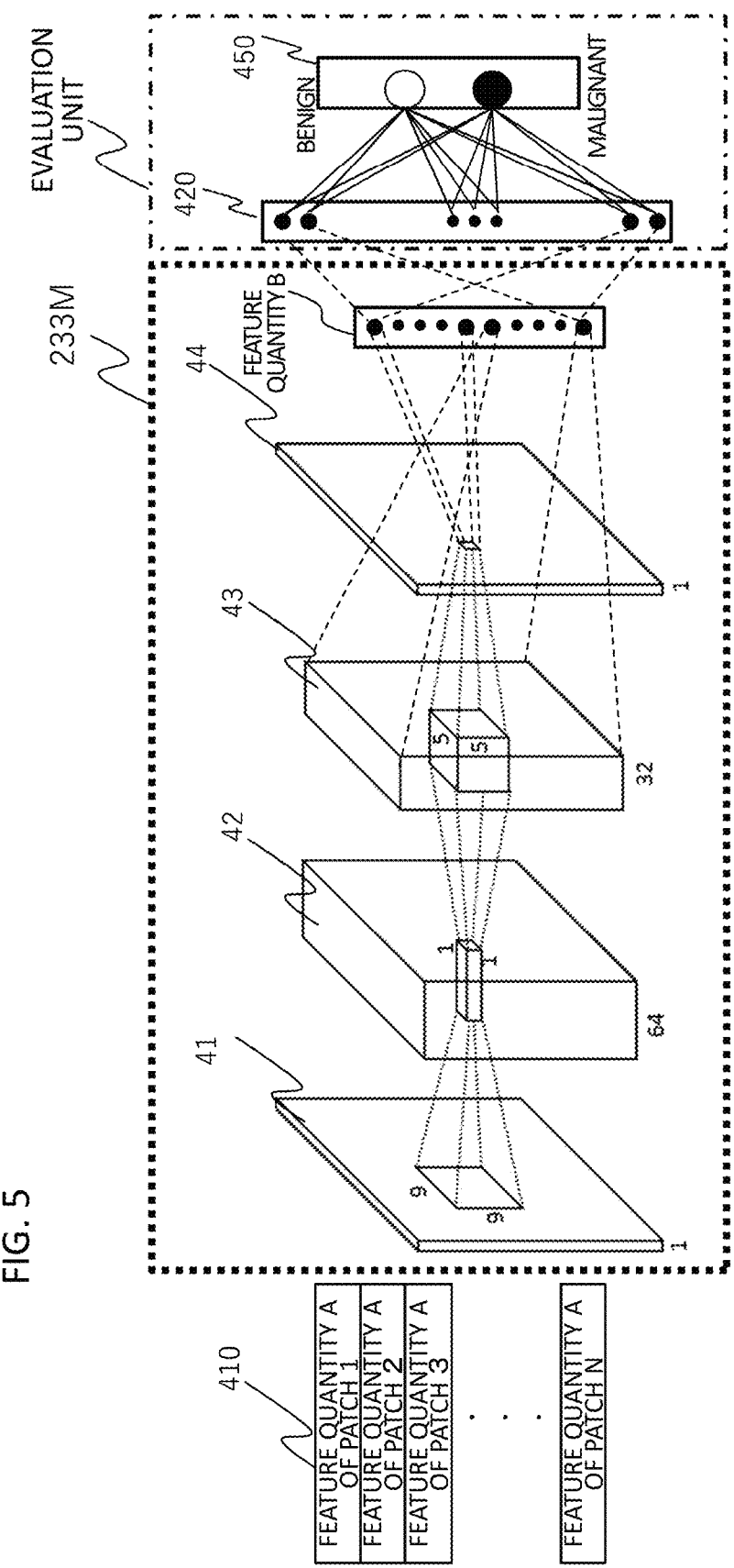
FIG. 5 is a diagram illustrating an example of a structure of a feature quantity abstraction unit (CNN)

FIG. 5 illustrates a configuration example of a CNN of this predictive model 233M. In the illustrated example, similar network architecture to that of FIG. 4 is used, and description of each layer is as described above. However, as the configuration of the CNN network, a known architecture (AlexNet, VGG-16, VGG-19, etc.) or a model obtained by pre-learning the architecture may be used as in the CNN 232M of the first model.

The CNN is trained so that a feature quantity that most contributes to the parameter is output, and is used as the predictive model 233M of the feature quantity abstraction unit 233.

Next, a description will be given of a third model used in the feature quantity conversion unit 234, which is a feature quantity conversion model 234M for converting the feature quantity B into the feature quantity C.

Figure 6:
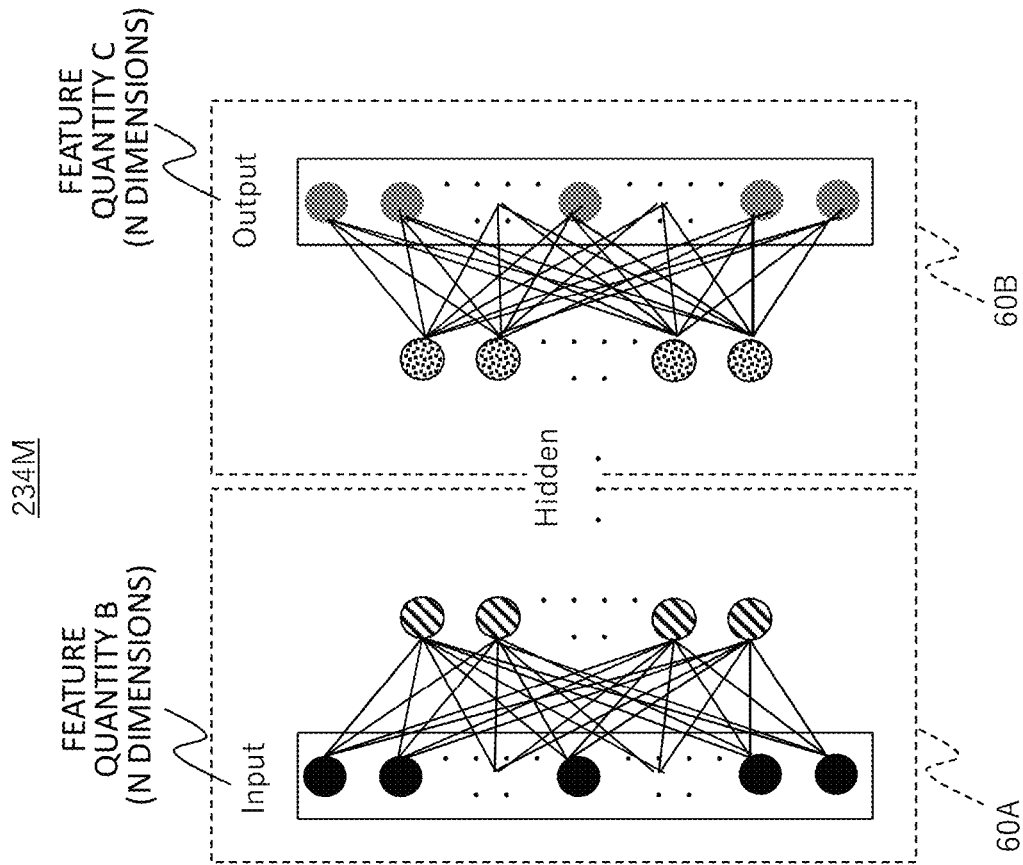
FIG. 6 is a diagram illustrating an outline of a structure of a feature quantity conversion unit (CNN)

As illustrated in FIG. 6, the feature quantity conversion model 234M includes two networks of an encoder 60A and a decoder 60B. This model is a model learned using the feature quantity B (for example, 1,024 dimensions) output from the feature quantity abstraction unit 233 as an input and using the feature quantity C (for example, 1,024 dimensions) as teacher data. The feature quantity C is a feature quantity separately extracted from an image of a different type from the medical image (first image) from which the feature quantity B is extracted, for example, a learning pathological image.

Figure 7:
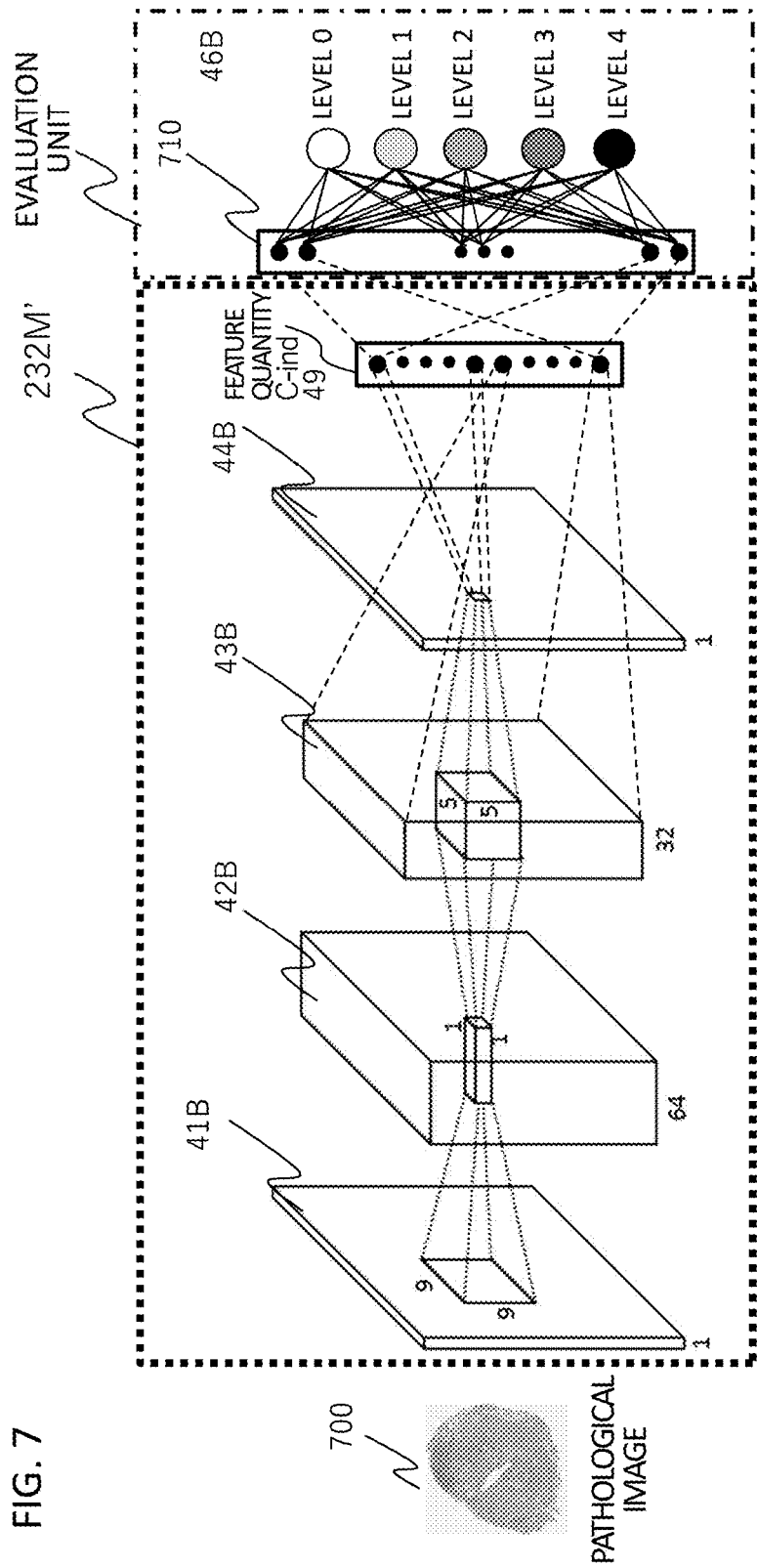
FIG. 7 is a diagram illustrating an example of a structure of a CNN for extracting a feature quantity C.
Figure 8:
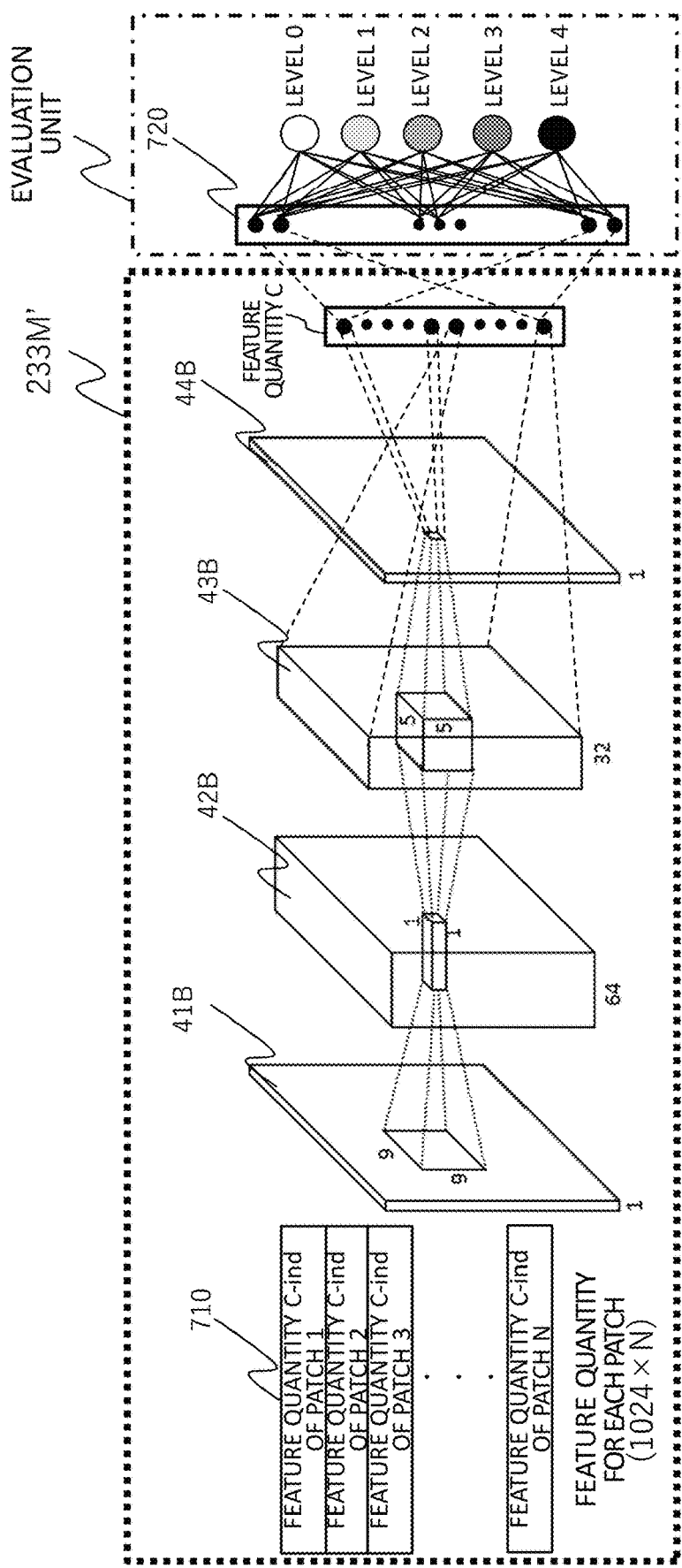
FIG. 8 is a diagram illustrating an example of a structure of a CNN for abstracting a feature quantity C.

The feature quantity C for learning used in the feature quantity conversion model 234M is extracted from the learning pathological image by a CNN. For example, as illustrated in FIG. 3B, the learning pathological image 700 generated by the pathological examination of the subject and subjected to patch processing is input to the CNN (FIG. 7) similar to the CNN illustrated in FIG. 4, a feature quantity is extracted, and a feature quantity C 710 is obtained for each patch. The feature quantity C 710 for each patch is further input to another CNN (FIG. 8) to finally extract, for example, a feature quantity 720 (for example, 1,024 dimensions) for accurately identifying a grade of a tumor part of the pathological image 700. Respective layers 41B to 44B of the CNN illustrated in FIGS. 7 and 8 are similar to the layers 41 to 44 of the CNN illustrated in FIGS. 4 and 5, and a description thereof will be omitted here.

A process of obtaining the learning feature quantity C using such a CNN may be performed as a process in the image processing unit 200 (diagnosis support processing unit 230), or may be performed by an arithmetic unit different from the image processing unit 200. In the case of performing using the image processing unit 200, a second image processing unit is added to the configuration of FIG. 2, patch processing using the pathological image (second image), feature quantity extraction, and feature quantity abstraction are performed here, and the feature quantity obtained by the feature quantity abstraction is used as the learning feature quantity C of the feature quantity conversion model.

When the feature quantity B is input to the encoder 60A of FIG. 6 using the learning feature quantity C prepared in this way, the feature quantity conversion model 234M used in the feature quantity conversion unit 234 is obtained by performing learning so that the feature quantity C 710 is output from the decoder 60B. The feature quantity conversion model 234M is not a model that learns a relationship between an image and a text as in the previous research (Elizabeth S. Burnside et al., "Using computer extracted image phenotypes from tumors on breast magnetic resonance imaging to predict breast cancer pathologic stage.", Cancer, 2016, p. 748-757) described above, and is characterized by learning a relationship between an image and an image and between feature quantities having a high degree of abstraction using the DL. In this way, conversion accuracy increases.

Note that even though FIG. 6 illustrates an example in which both the feature quantity B and the feature quantity C are N dimensions (N is a natural number), dimensions thereof may not be the same. For example, when the feature quantity B has N dimensions and the feature quantity C has M dimensions, the number of dimensions of the feature quantity C may be larger than the number of dimensions of the feature quantity B (M>N) or may be smaller than the dimension of the feature quantity B (M<N).

Figure 9:
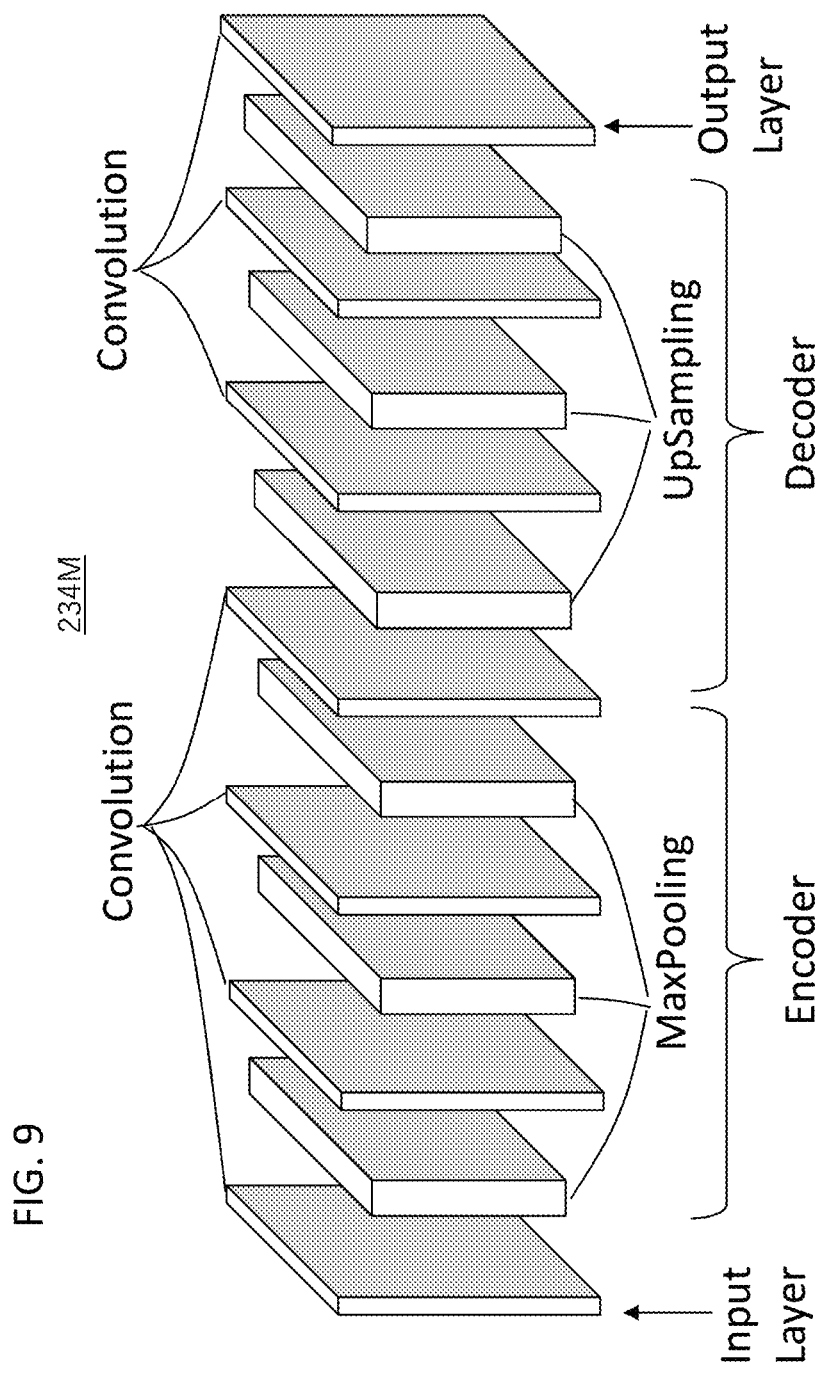
FIG. 9 is a diagram illustrating details of the structure of the feature quantity conversion unit.

For example, as illustrated in FIG. 9, the CNN of the feature quantity conversion model 234M has a multi-layer structure in which a convolutional layer and a pooling layer, and a convolutional layer and an upsampling layer are stacked. An example of processing in each layer is as shown in Table 1 below.

TABLE 1

Example of content of each treatment

| Classification | Network | Activation function | Output ch (deepness of feature map) | Convolution filter size | Treatment |
|---|---|---|---|---|---|
| Encoder | Stage 1 | ReLu | 16 | 3 | Convolution(1D) |
| | Downsampling | | | | MaxPooling(1D) |
| | Stage 2 | ReLu | 8 | 3 | Convolution(1D) |
| | Downsampling | | | | MaxPooling(1D) |
| | Stage 3 | ReLu | 8 | 3 | Convolution(1D) |
| | Downsampling | | | | MaxPooling(1D) |
| Decoder | Stage 1 | ReLu | 8 | 3 | Convolution(1D) |
| | Upsampling | | | | UpSampling(1D) |
| | Stage 2 | ReLu | 8 | 3 | Convolution(1D) |
| | Upsampling | | | | UpSampling(1D) |
| | Stage 3 | ReLu | 16 | 3 | Convolution(1D) |
| | Upsampling | | | | UpSampling(1D) |
| Output | | Sigmoid | 1 | 3 | Convolution(1D) |

Figure 10:
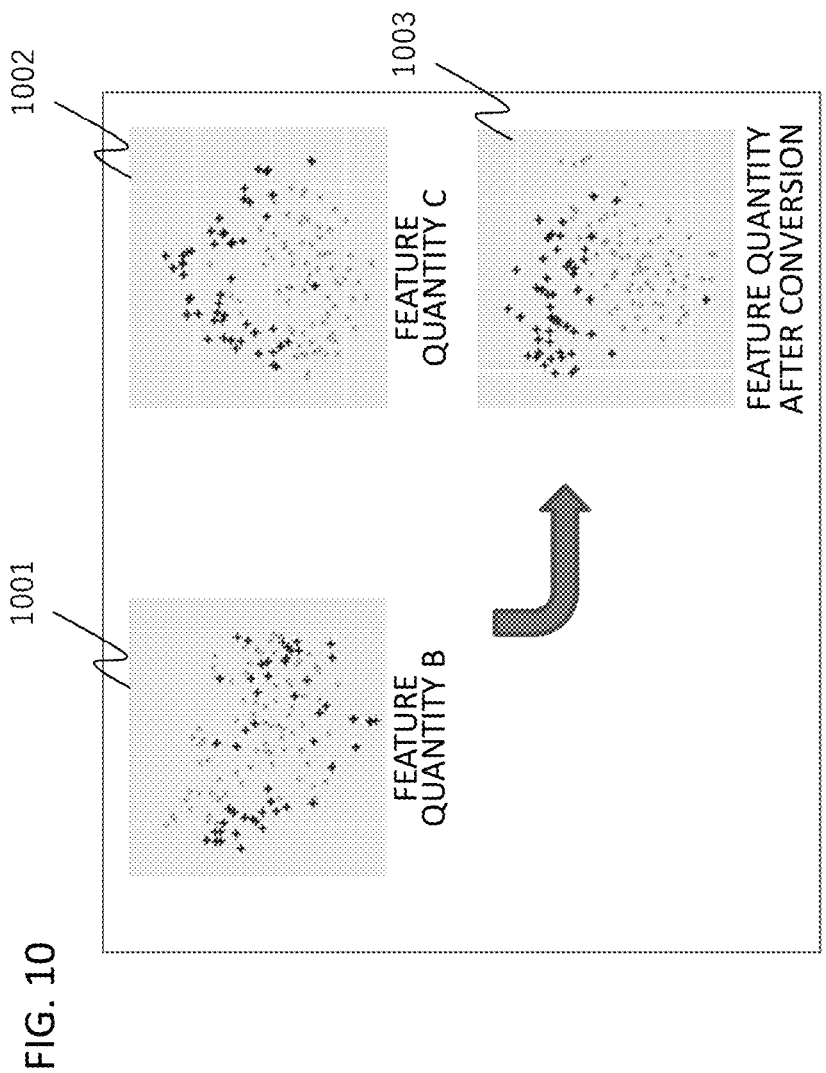
FIG. 10 is a diagram illustrating an example of feature quantity conversion.

FIG. 10 illustrates an example of a result of feature quantity conversion in the present embodiment. A feature quantity map 1001 is a map of the feature quantity B, a feature quantity map 1002 is a map of the feature quantity C, and a feature quantity map 1003 is a map generated from the feature quantity B by the feature quantity conversion. These maps are obtained by compression from multidimensional (1,024 dimensions) ones to two-dimensional ones by t-distributed Stochastic Neighbor Embedding (tSNE). From FIG. 10, it can be understood that the map 1003 obtained by the feature quantity conversion has characteristics close to those of the map 1002 of the feature quantity C that is teacher data.

Next, a description will be given of a fourth identification model 235M used in the identification unit 235. This model calculates a predetermined parameter value from a feature quantity after conversion, and predicts the presence or absence of a lesion site, malignancy, etc. represented by the parameter value.

Figure 11:
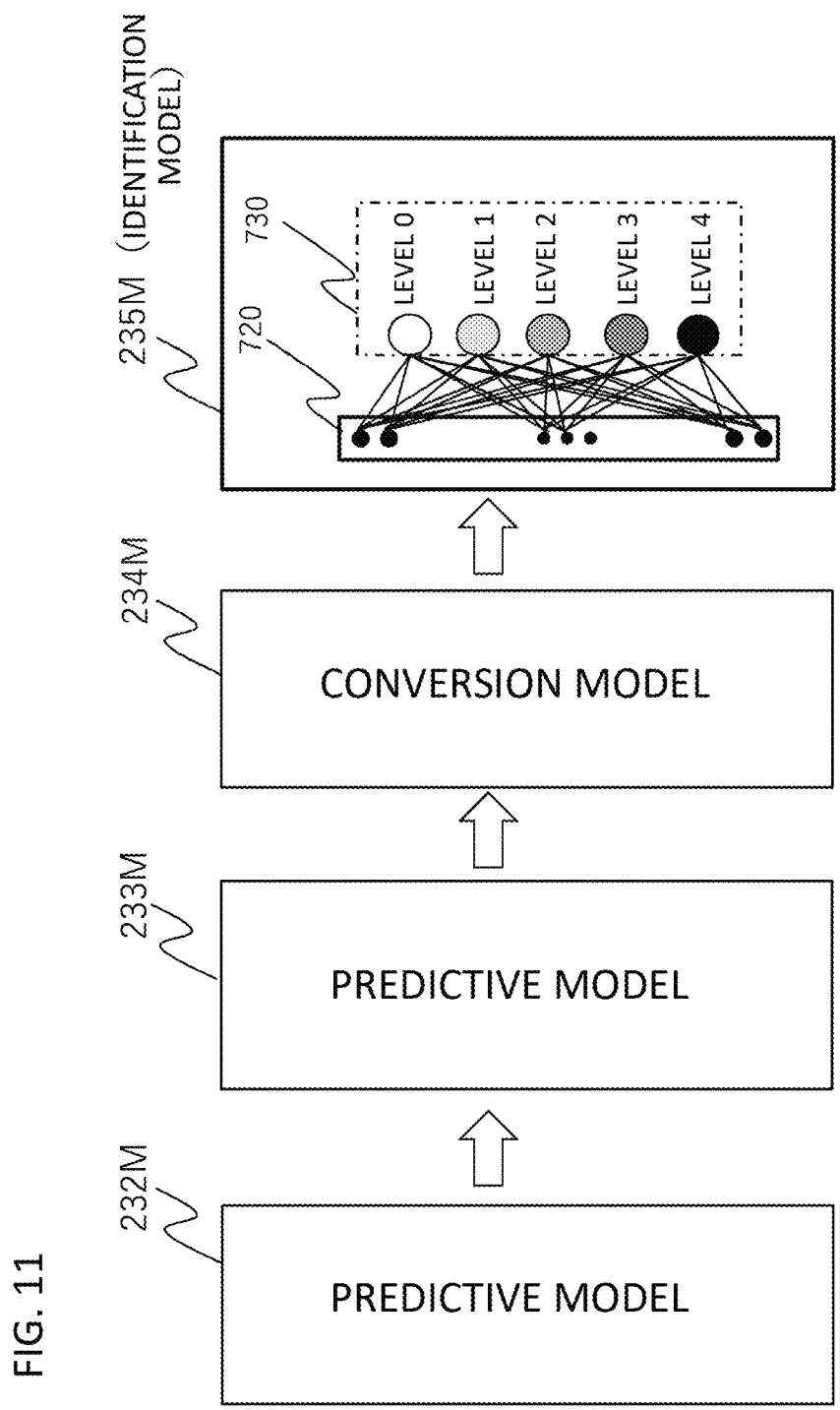
FIG. 11 is a diagram illustrating an example of a structure of an identification unit.

For example, as illustrated in FIG. 11, the identification model 235M can be implemented by a CNN trained so that the feature quantity C 710 is input and a grade 730 of malignancy is output. As the CNN of the identification model, for example, it is possible to use known software (OSS: Open Source Software) such as TensorFlow (Google (registered trademark)), Chainer (Preferred Networks (registered trademark)), Theano (Universite de Montreal), etc.

The identification model 235M is incorporated in the identification unit 235 such that such a CNN is trained using a plurality of combinations of the feature quantity (feature quantity C) after conversion and a grade 9 of tumor malignancy as learning data and a grade closest to a grade classified from the feature quantity C is extracted when the feature quantity C is input to the identification unit 235. In the example illustrated in FIG. 11, the feature quantity C 720 is divided into a plurality of categories necessary for diagnosis, and a grade of tumor malignancy (for example, level 0 to level 4) is calculated as a parameter 730 from this category.

[Design of Error Function]

Next, a description will be given of an error function used when the predictive model or the identification model described above is created by learning of the CNN. The error function is used to evaluate a difference between an output and teacher data when the CNN is trained. The error function is generally based on an error propagation method represented by Formula (1).

[Equation 1]

$$E = \sum_k \frac{(t_k - y_k)^2}{2} \quad (1)$$

$t_k$: Teacher data
$y_k$: Network output data

Even though the error function of Formula (1) can be used in the present embodiment, any of the following error functions or a combination thereof can be used, which can improve the accuracy of the predictive model.

1. Predetermined spatial distance error
2. Identification model error
3. Medical knowledge incorporated error Hereinafter, these error functions will be described.

1. Predetermined Spatial Distance Error

Figure 12:
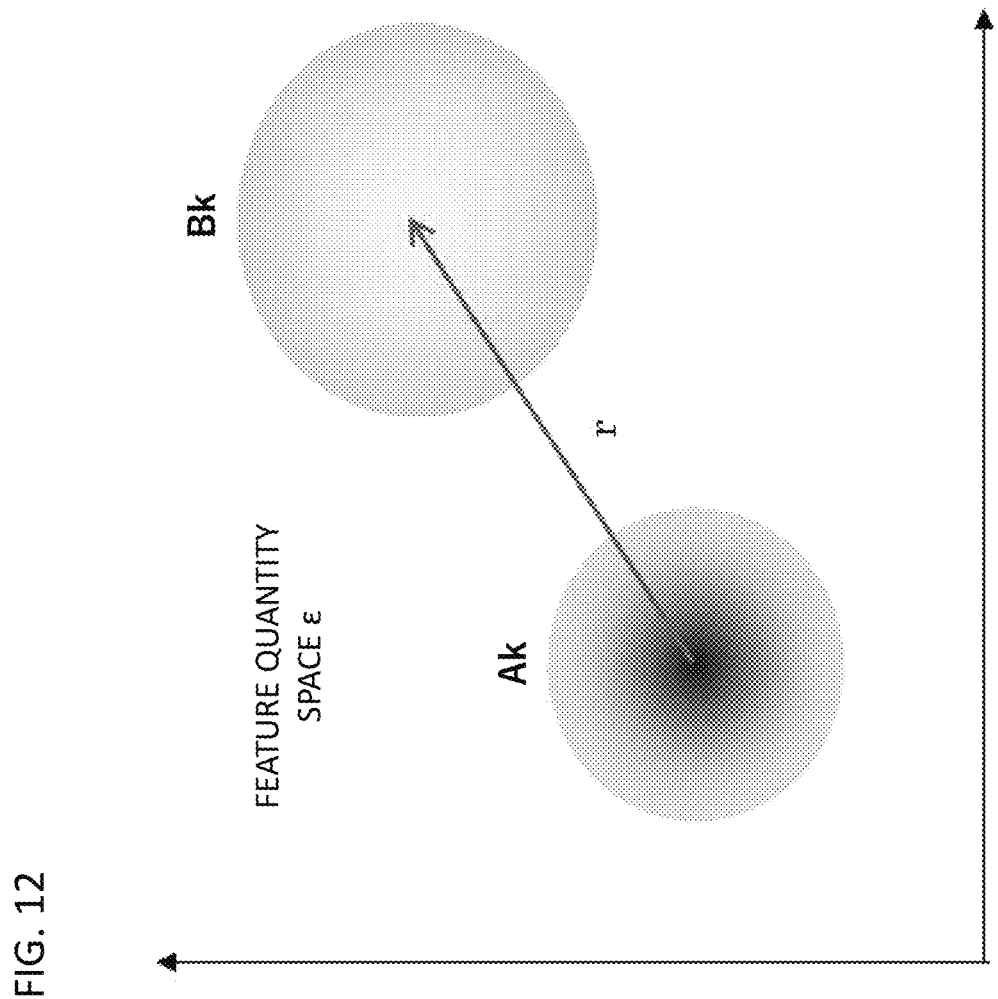
FIG. 12 is a diagram for description of an example of an error function in a feature quantity space.

When data of the feature quantity A and data of the feature quantity B for learning are set to an input (teacher data) $A_k$ and an output $B_k$, respectively, each of the teacher data $A_k$ and the output $B_k$ is dimensionally transformed and compressed and mapped to a predetermined space ε as illustrated in FIG. 12. As a mapping method, for example, principal component analysis (PCA) or t-distributed Stochastic Neighbor Embedding (tSNE) is used. Note that even though the space ε is set to a two-dimensional space in this figure, the invention is not limited thereto.

By adding a distance r between the teacher data $A_k$ and the output $B_k$ on the space ε (for example, between the centers of gravity of the respective data sets) to the error function of Formula (1), an error function is set so that an error of the distance r on the space ε becomes small. For example, when a conversion function to the space ε is set to g and the center of gravity (average value of coordinates of each piece of data) on the space ε is represented by C, the error function is represented by the following Formula (2).

[Equation 2]

$$E2 = \sum_k \frac{(C(g(A_k)) - C(g(B_k)))^2}{2} \quad (2)$$

The feature quantity abstraction unit 233 and the feature quantity conversion unit 234 carry out learning by an error back propagation method using Formula (2) as an error function.

2. Identification Model Error

Figure 13:
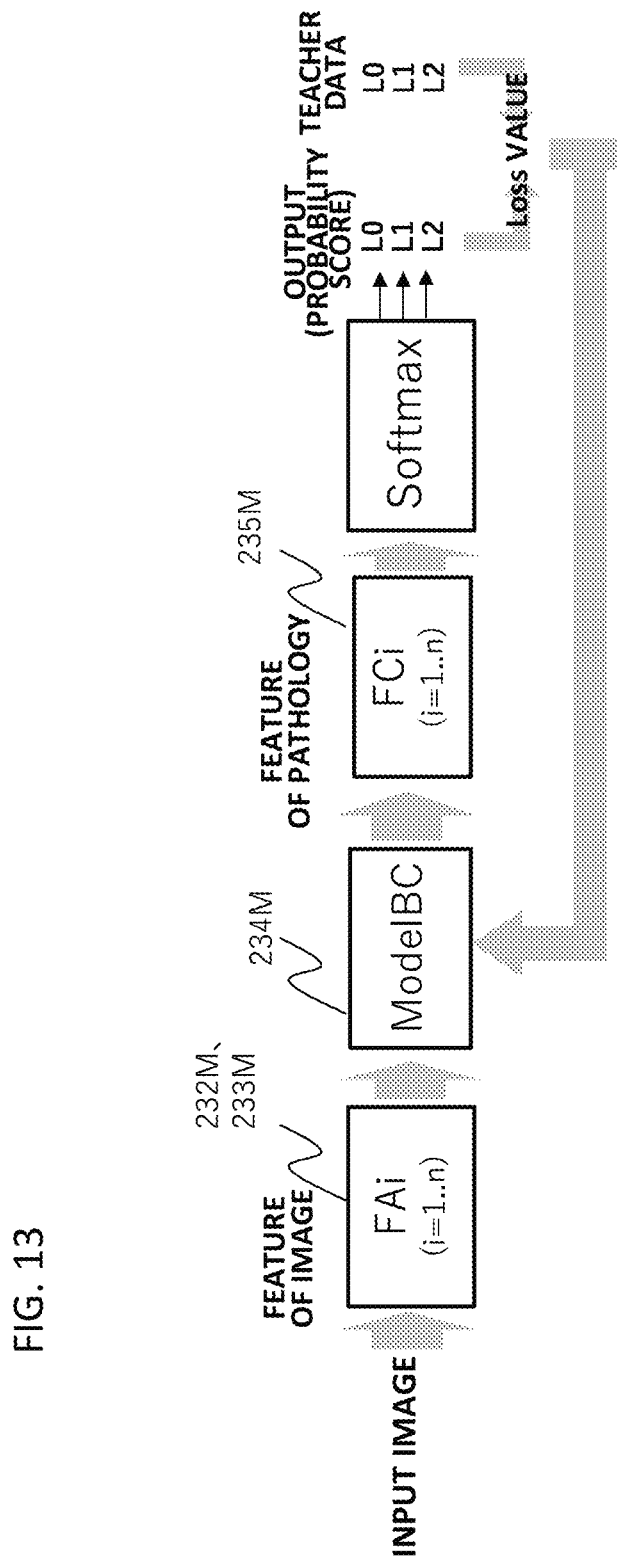
FIG. 13 is a diagram for description of another example of the error function.

As illustrated in FIG. 13, this error function is an error function that minimizes an identification result by back-propagating an error (loss value) between an output from the identification model 235M and the teacher data when learning the feature quantity conversion model 233M and the identification model 234M (model including an identification result performed by the identification unit 235 in addition to the feature quantity conversion model of the feature quantity conversion unit 234). A method using this error function adopts a configuration in which learning is performed in a form of connecting the CNNs included in the four models described above, that is, in an end-to-end form.

In this method, first, a loss function is set using a difference between an output (probability score: Softmax layer output (0-1)) for each identification class in the identification unit 235 and teacher data as a loss value. When the number of classes of the output of the identification result is three as illustrated in FIG. 13, an output vector ($y_{L1}$, $Y_{L1}$, $Y_{L2}$) has values represented by the following Formula (3).

[Equation 3]

$$\begin{pmatrix} y_{Lo} \\ y_{L1} \\ y_{L2} \end{pmatrix} = \begin{pmatrix} 0.6 \\ 0.2 \\ 0.2 \end{pmatrix} \quad (3)$$

Meanwhile, a teacher data vector ($Y0_{L1}$, $Y0_{L1}$, $Y0_{L2}$) has values represented by the following Formula (4).

[Equation 4]

$$\begin{pmatrix} yo_{Lo} \\ yo_{L1} \\ yo_{L2} \end{pmatrix} = \begin{pmatrix} 1 \\ 0 \\ 0 \end{pmatrix} \quad (4)$$

A vector error between the output vector and the teacher data vector can be defined as an error function such as the following Formula (5).

[Equation 5]

$$E3 = -\sum_{k=L0}^{L2} yo_k \log y_k \quad (5)$$

Figure 14:
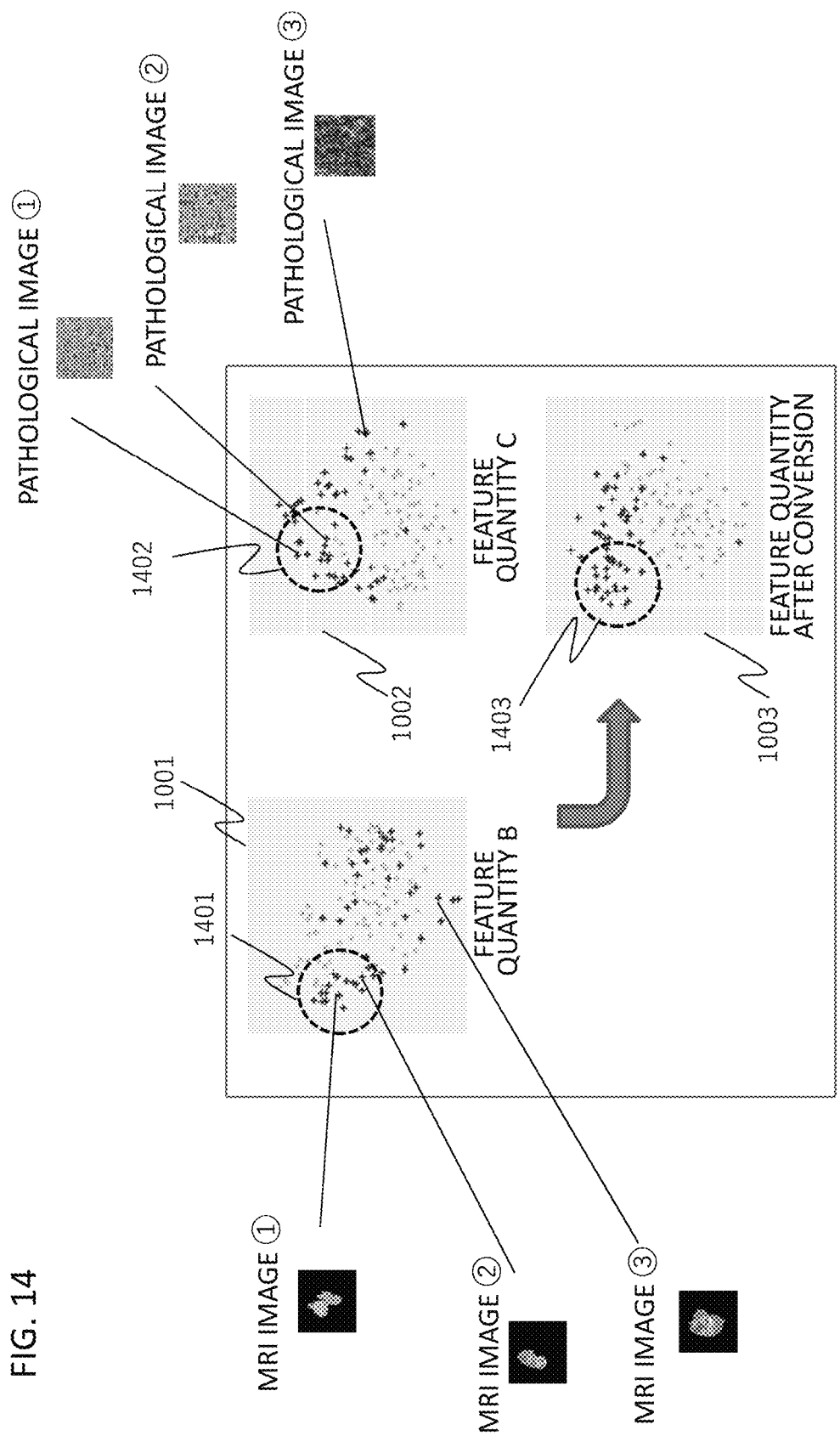
FIG. 14 is a diagram for description of a relationship between feature quantities in the feature quantity space.

When the values of the output vector and the teacher data vector are used, a value of Formula (5) becomes $E3 = -(1 \times \log 0.6 + 0 \times \log 0.2 + 0 \times \log 0.2) =$ $-(-0.22) =$ $0.22$ 3. Medical Knowledge Incorporated Error This error function is a combination of the above-mentioned predetermined spatial distance error and medical knowledge. The predetermined spatial distance error defines an error function that brings the entire space closer, using a center of gravity of a feature quantity space as a parameter. In this error function, a space to be matched is weighted based on medical knowledge and importance. Specifically, as illustrated in FIG. 14, in the feature quantity space (feature quantity map), a relationship in image data among teacher data 1002, image data before conversion 1001 and after conversion 1003 from the feature quantity B to the feature quantity C is analyzed. For example, a feature quantity space error reduction is particularly weighted to the distance between a patch image (group) 1402 having a deep relation to determination of the presence or absence of a disease in a pathological image and an MRI image (group) 1401 corresponding thereto.

In the feature quantity map illustrated in FIG. 14, each point (feature) corresponds to an individual patch (MR image 1, 2, 3, etc.). A patch included in the group before conversion 1401 moves to a group 1403 of the map after conversion 1003 after feature quantity conversion, and this region corresponds to a region of the group 1402 (pathological images 1 and 2) having high importance in the pathological image. As described above, which patch in the map 1001 is highly related to the group 1402 of the map 1002 can be known by analyzing a position to which each patch moves in the feature quantity map after conversion 1003. The accuracy of learning can be further improved by weighting a spatial distance between highly related regions to reduce an error. Processing is similar to the predetermined spatial distance error, in which coordinates (centers of gravity) of patch images (groups) highly related to each other are obtained from medical knowledge, and an error between the coordinates (centers of gravity) is defined as an error function.

Figure 15:
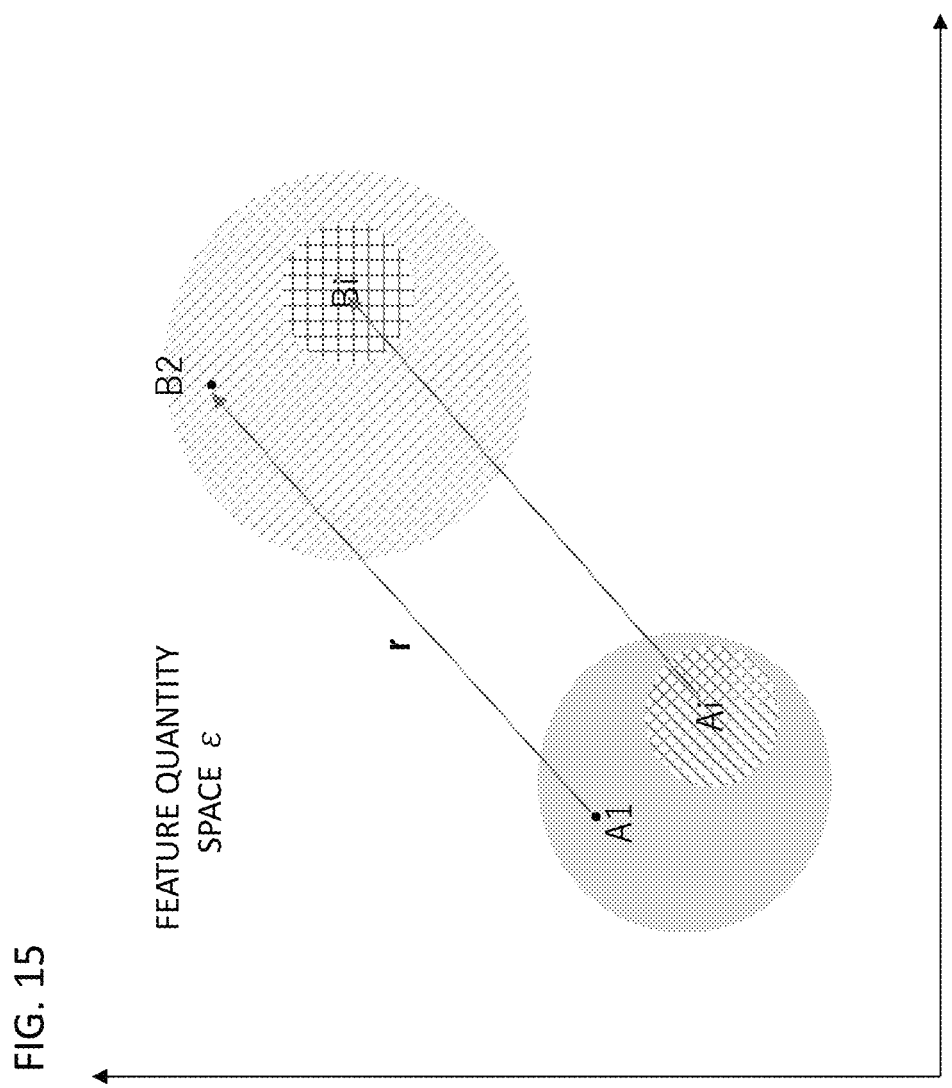
FIG. 15 is a diagram for description of still another example of the error function in the feature quantity space.

For example, in FIG. 15 illustrating a feature quantity space, an error function in which weights are given to a distance between medically important teacher data A1 and an output B1 and a distance between next important teacher data group (data set S) Ai and an output Bi is set. When a conversion function to the feature quantity space ε is set to g and the center of gravity (average value of coordinates of each piece of data) on the space ε is represented by C, the error function is represented by the following Formula (6).

[Equation 6]

$$E4 = \frac{\alpha(g(A1) - g(B1))^2}{2} + \beta\left(\sum_{i \in S} \frac{(C(g(Ai)) - C(g(Bi)))^2}{2}\right) + \gamma\left(\sum_{k \notin S} \frac{(C(g(Ak)) - C(g(Bk)))^2}{2}\right) \quad (6)$$

Here, α, β, and γ are weighting factors, for example, α=0.5, β=0.4, and γ=0.1.

By using the error function as described above, it is possible to reduce the error of the feature quantity conversion model or the identification model and realize a more accurate predictive model. Alternatively, the error functions (2) and (5) may be combined and weighted to form an error function represented by the following Formula (7).

[Equation 7]

$$E5 = w1*E2 + w2*E3 \quad (7)$$

Here, w1 and w2 are weighting factors (for example, w1=0.5, w2=0.5). Similarly, (5) and (6) may be combined.

The four models learned as described above are predictive models or identification models used in the diagnosis support processing unit 230. These four models can be incorporated in the diagnosis support processing unit 230 as one combined model, and in this case, each learned model portion of the combined model corresponds to each unit included in the diagnosis support processing unit.

[Image Processing Operation]

Figure 16:
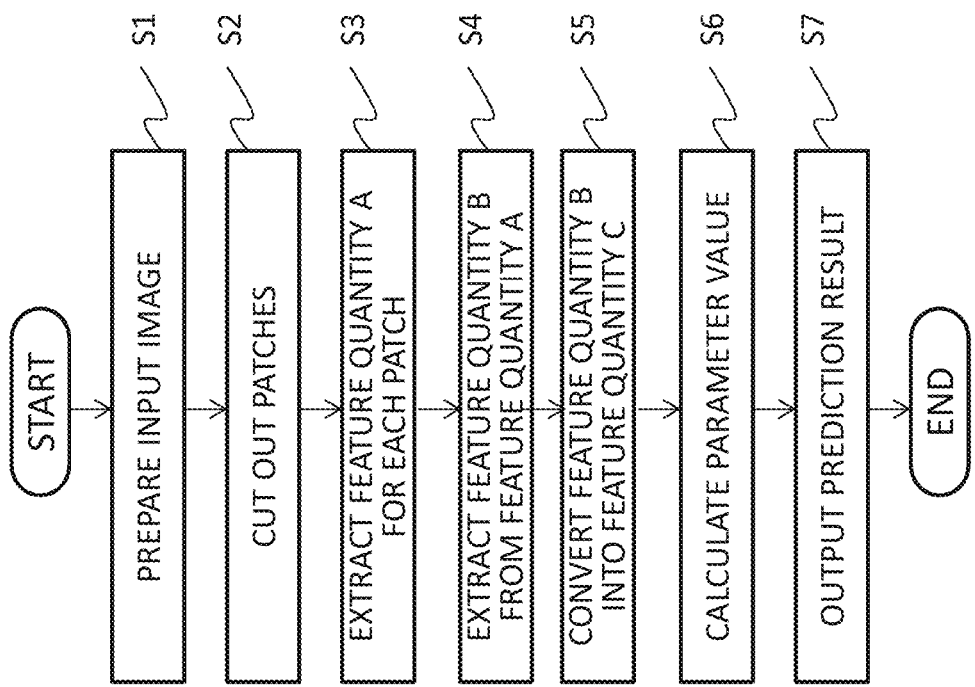
FIG. 16 is a diagram illustrating a flow of an operation of an image processing unit incorporating a learning model.

Next, a description will be given of a flow of operation of the image processing unit 200 in which the learned predictive model described above is incorporated with reference to FIG. 16 using the case of cutting out patches as an example.

Upon receiving an image signal from the imaging unit 100, the image processing unit 200 first prepares an input image to be processed by the diagnosis support processing unit 230. Specifically, the image reconstructing unit 210 generates image data of the input image from the image signal, the correction processing unit 220 corrects the image using the generated image data as necessary, and the corrected image data is passed to the diagnosis support processing unit 230 (S1). Further, the correction processing unit 220 sends the corrected image data to the output unit 120.

Subsequently, the patch processing unit 231 cuts out all the image data to be processed into patches of a predetermined size (FIG. 3A), and passes the patches to the feature quantity extraction unit 232 (S2), as in the creation of the predictive model. The feature quantity extraction unit 232 extracts the feature quantity A of the input image 400 for each patch using the predictive model 232M (FIG. 4) (S3). Subsequently, the feature quantity abstraction unit 233 extracts the feature quantity B abstracted from the feature quantity A using the predictive model 233M (FIG. 5) (S4).

Subsequently, the feature quantity conversion unit 234 uses the feature quantity conversion model 234M (FIG. 6) to convert the feature quantity B into the feature quantity C (S5). The identification unit 235 uses the identification model 235M to calculate a parameter value for predicting and identifying a disease from the converted feature quantity C (S6), and outputs a prediction result to the output unit 120 (S7).

Figure 17A:
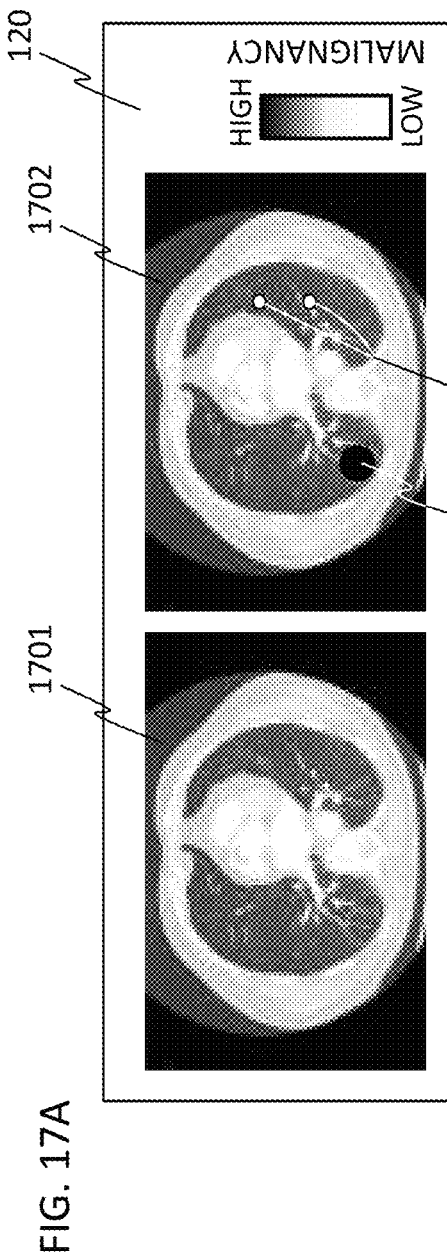
FIGS. 17A and 17B are diagrams illustrating display examples of an input image and an output image, respectively.

Through the above operation, as illustrated in FIG. 17, each of image data 1702 of an image 1701 corrected by the correction processing unit 220 and image data of an image 1702 obtained by superimposing a processing result of the diagnosis support processing unit 230 on the image 1701 is output to the output unit 120, and one or both of the images 1701 and 1702 are displayed. The output unit 120 may display the parameter value output from the diagnosis support processing unit 230.

A method of displaying the parameter value in the output unit 120 is not limited to a specific method as long as a user of the medical imaging apparatus 10 can recognize the parameter value, and examples thereof include a method of displaying a mark, a numerical value, an image, etc.

Figure 17B:
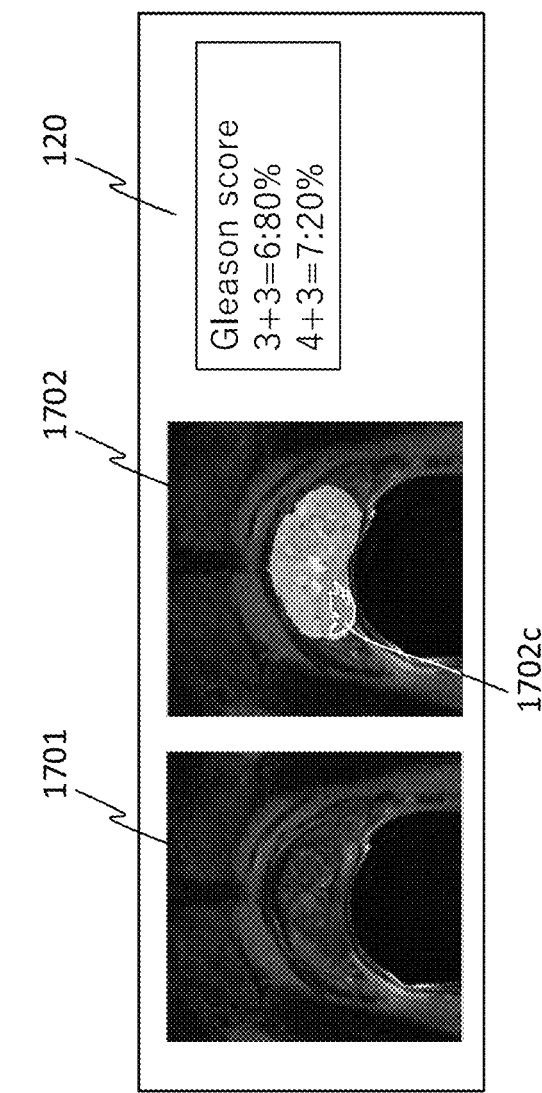

When the parameter is the malignancy of the tumor, it is possible to form the image 1702 by superimposing a mark according to the malignancy on a site of the tumor in the image 1701. For example, in the image 1702 illustrated in FIG. 17A, the color of the mark to be superimposed on the image is changed according to the malignancy, and a high malignancy part 1702a is black and a low malignancy part 1702b is white. In addition, when the parameter is GS, etc. used for stage calculation of prostate cancer, as illustrated in FIG. 17B, a region 1702c having a tumor may be surrounded and presented, or information (numerical value) indicating GS may be displayed. Furthermore, as illustrated in FIG. 17B, a pathological image of the same site predicted from the parameter value may be superimposed and displayed on the site having the disease.

As described above, according to the present embodiment, the input image may be generated from the signal collected by the imaging unit 100, and the feature quantity A and the feature quantity B extracted from the input image can be converted into the feature quantity C of the image having more detailed information to calculate the parameter value used for more accurate diagnosis from the feature quantity C. In this way, it is possible to present more accurate diagnosis support information using the medical imaging apparatus. More specifically, the disease can be predicted based on the feature of the pathological image by only inputting the image acquired by the medical imaging apparatus such as the MRI image, and the information collection cost can be reduced.

Further, in the present embodiment, since a relationship between feature quantities of different images is learned, for example, it is possible to medically show which part of an image of the medical imaging apparatus is used for determining a feature obtained in a pathological image. Thus, it is possible to more accurately make determination of the user on a diagnosis result. In other words, it is possible to allow the user to notice a feature that is generally difficult to see in the image of the medical imaging apparatus and may be overlooked.

First Modification of First Embodiment

Figure 18A:
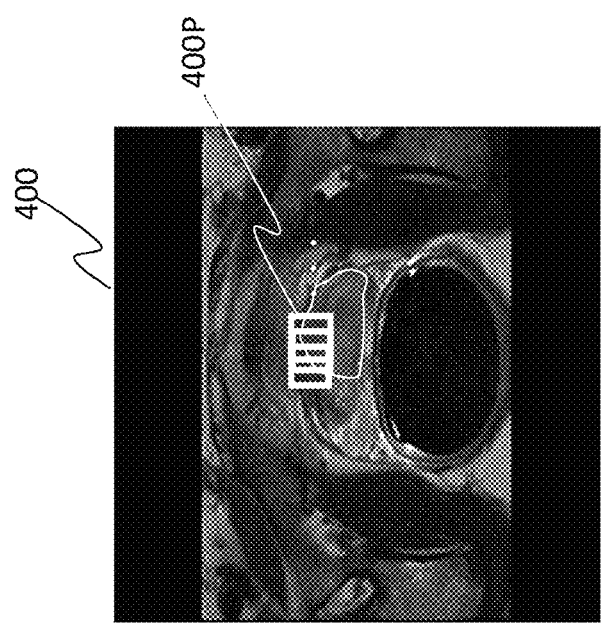
FIGS. 18A and 18B are diagrams for description of patch processing of a first modification of the first embodiment.

In the first embodiment, the patches are cut out from the image data under the condition that the respective patches do not overlap each other. However, the patch processing unit 231 may cut out a patch 400P so that adjacent patches overlap each other as illustrated in FIG. 18A. The image quality of the output image can be further improved by overlapping and cutting out the patches and performing the CNN processing as described above. Note that instead of overlapping all patches, only some patches, for example, patches in a region of interest (ROI) may be overlapped.

Figure 18B:
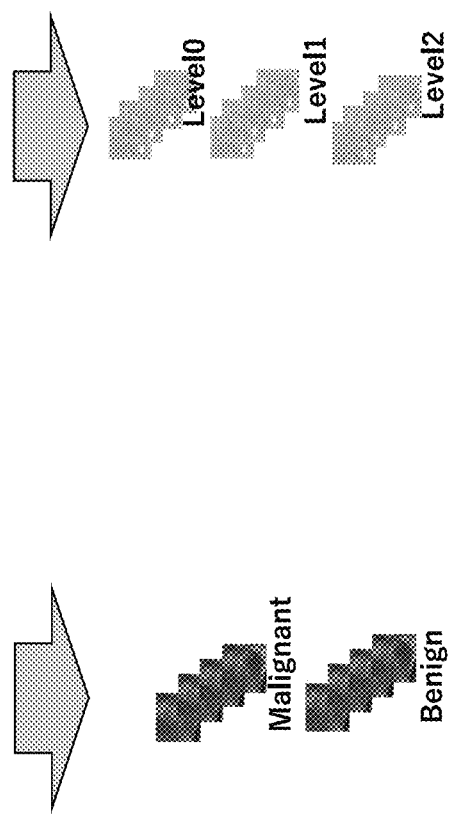

When the feature quantity C is extracted from the second image 700, a patch 700P may be cut out so as to have an overlap as illustrated in FIG. 18B.

Second Modification of First Embodiment

All the patches cut out from the image data by the patch processing unit 231 may be processed. However, only an image in an ROI may be processed.

Figure 19:
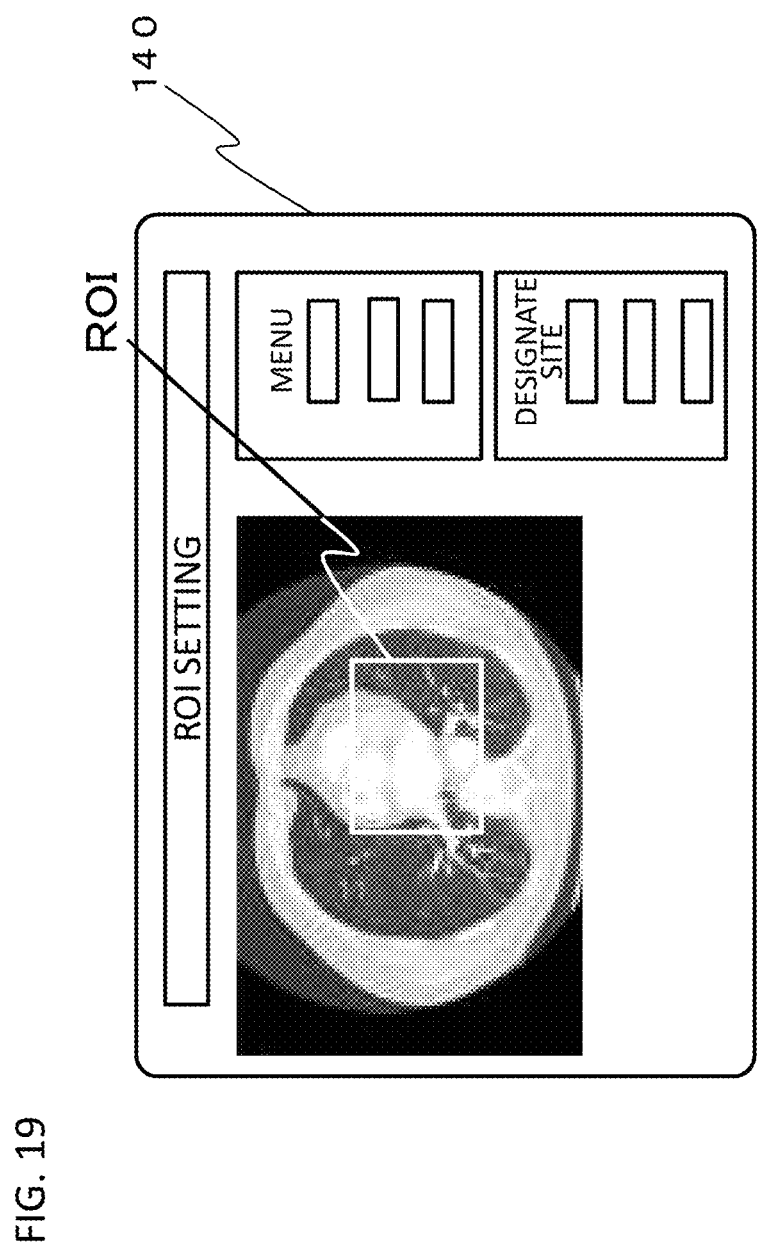
FIG. 19 is a diagram illustrating a screen example of ROI setting according to a second modification of the first embodiment.

In this case, for example, it is possible to cause the output unit 120 to display a UI (ROI setting unit 140), etc. illustrated in FIG. 19, so that the user sets the ROI through the UI. When the user sets the ROI, the image processing unit 200 uses the information to process only image data of a part set to the ROI. In this way, for example, only the lesion and the vicinity thereof can be processed, the processing time of prediction can be shortened, and the accuracy of prediction can be improved.

As described above, according to the present modification, by omitting image processing of the part outside the ROI, it is possible to reduce the processing time as a whole.

Third Modification of First Embodiment

In the first embodiment, an example in which a parameter (for example, tumor malignancy grade) is calculated from an input image has been described, but a type of parameter that can be output by the image processing unit is not limited to one type. For example, it is possible to store, in the storage device 130, a plurality of patterns of learning models such as a learning model according to an examination site of the subject such as breast cancer or gastric cancer, or a learning model according to various diseases other than the tumor. In this case, when the user inputs a diagnosis site, a disease name to be diagnosed, etc. from the input unit 110, a learning model used by the image processing unit 200 for processing is selected according to the input content, and a parameter is calculated using the selected learning model.

Second Embodiment

In the first embodiment, in extraction of the feature quantity B and the feature quantity C, each feature quantity is extracted from one type of image information. However, the present embodiment is different in that a feature quantity abstracted by combining feature quantities of a plurality of types of images is extracted. A difference between the process of the first embodiment and the process of the present embodiment will be described with reference to FIGS. 20 and 21 conceptually illustrating the processes. Here, as an example, a description will be given of the case where an image input to the diagnosis support processing unit is an image acquired the MRI apparatus. However, the invention is not limited thereto. For example, other modality images of the CT, X-rays, ultrasonic waves, etc. may be input.

Figure 20:
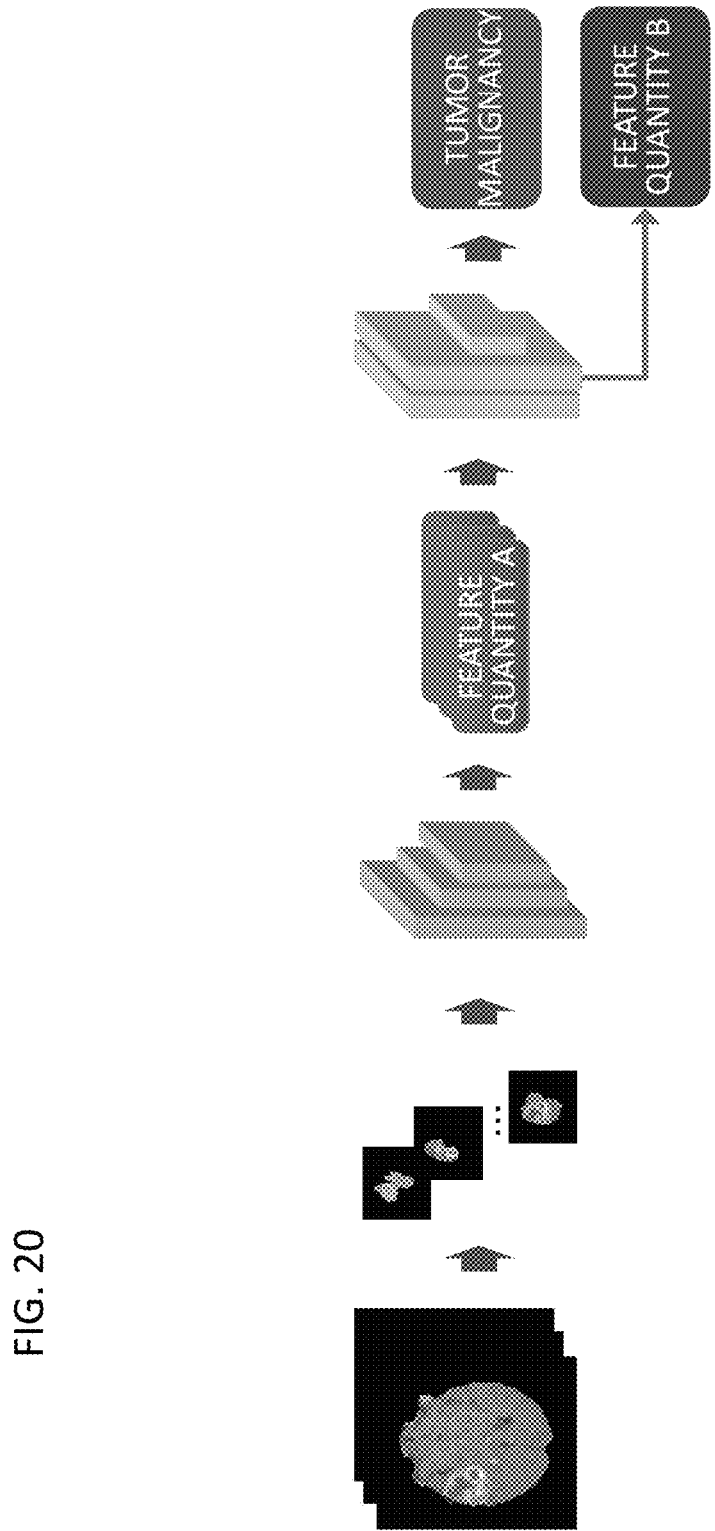
FIG. 20 is a diagram illustrating a process of extracting feature quantities A and B of the first embodiment.

In the process of the first embodiment, as illustrated in FIG. 20, for example, a relevant part of the lesion is cut out by a patch from a plurality of T1 weighted images of the MRI to extract the feature quantity A, and each feature quantity A obtained by each patch is combined to extract the feature quantity B particularly contributing to determination of the disease.

Figure 21:
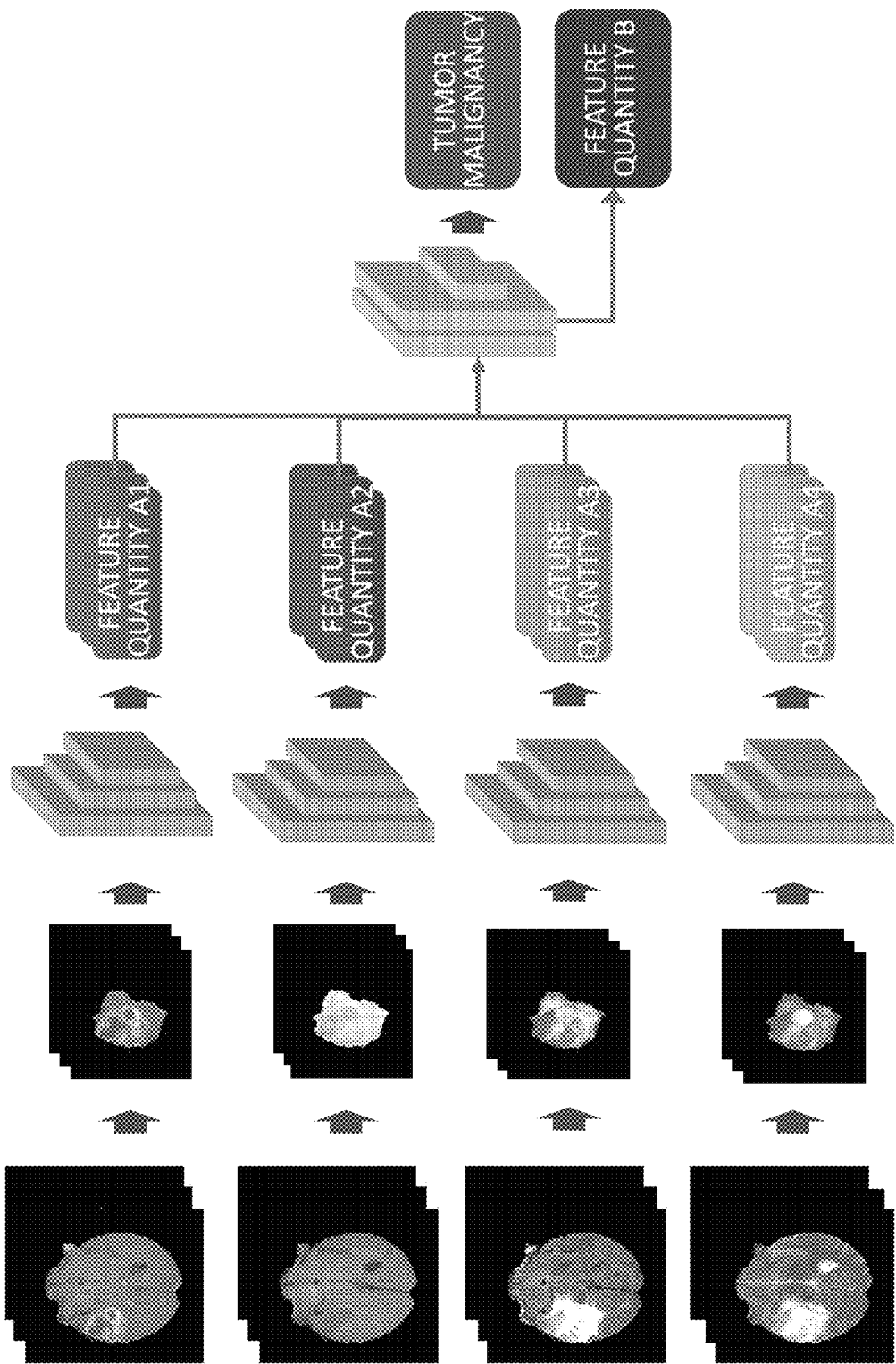
FIG. 21 is a diagram illustrating a process of extracting feature quantities A and B of a second embodiment.

On the other hand, in the present embodiment, as illustrated in FIG. 21, a plurality of types of MRI images, here, a T1 weighted image, a T2 weighted image, and images (such as a diffusion weighted image) having different image quality parameters are input, and the feature quantity A is extracted for each patch in each image. All of these feature quantities A are combined to extract the feature quantity B that particularly contributes to the determination of the disease. That is, in the diagnosis support processing unit 230 illustrated in FIG. 2, the patch processing unit 231 and the feature quantity extraction unit 232 are prepared for the number of types of images to be input (for example, M), and feature quantities as many as the number of patches (for example, L) are output from each feature quantity extraction unit 232 as the feature quantity A.

The feature quantity abstraction unit 233 inputs the feature quantity (the number of images×the number of patches) obtained by fusing the feature quantities A1 to A4 output from each feature quantity extraction unit 232, and outputs one feature quantity B. The fusion of the feature quantities A1 to A4 may be a simple combination thereof or addition may be performed. In this way, by inputting more information to the predictive model 233M of the feature quantity abstraction unit 233, it is possible to obtain a more reliable feature quantity B that is more effective for diagnosis.

A process after obtaining the feature quantity B is similar to that in the first embodiment. However, when obtaining the feature quantity C, a plurality of images may be used as another image. For example, the feature quantity C is extracted by adding another stained image such as IHC stain in addition to an HE stained image of the pathological image. In this way, with respect to the second image, the feature quantity C in which the feature of the lesion, that is the diagnosis target, is appropriately extracted can be obtained. As a result, the reliability of the parameter, which is the processing result of the diagnosis support processing unit 230, can be improved.

Note that even though FIG. 21 illustrates the case where the input is only an image, the input may be a feature quantity obtained by combining non-image information such as electronic medical record information, various text information, or vital data information.

Embodiment of Image Processing Apparatus

Figure 22:
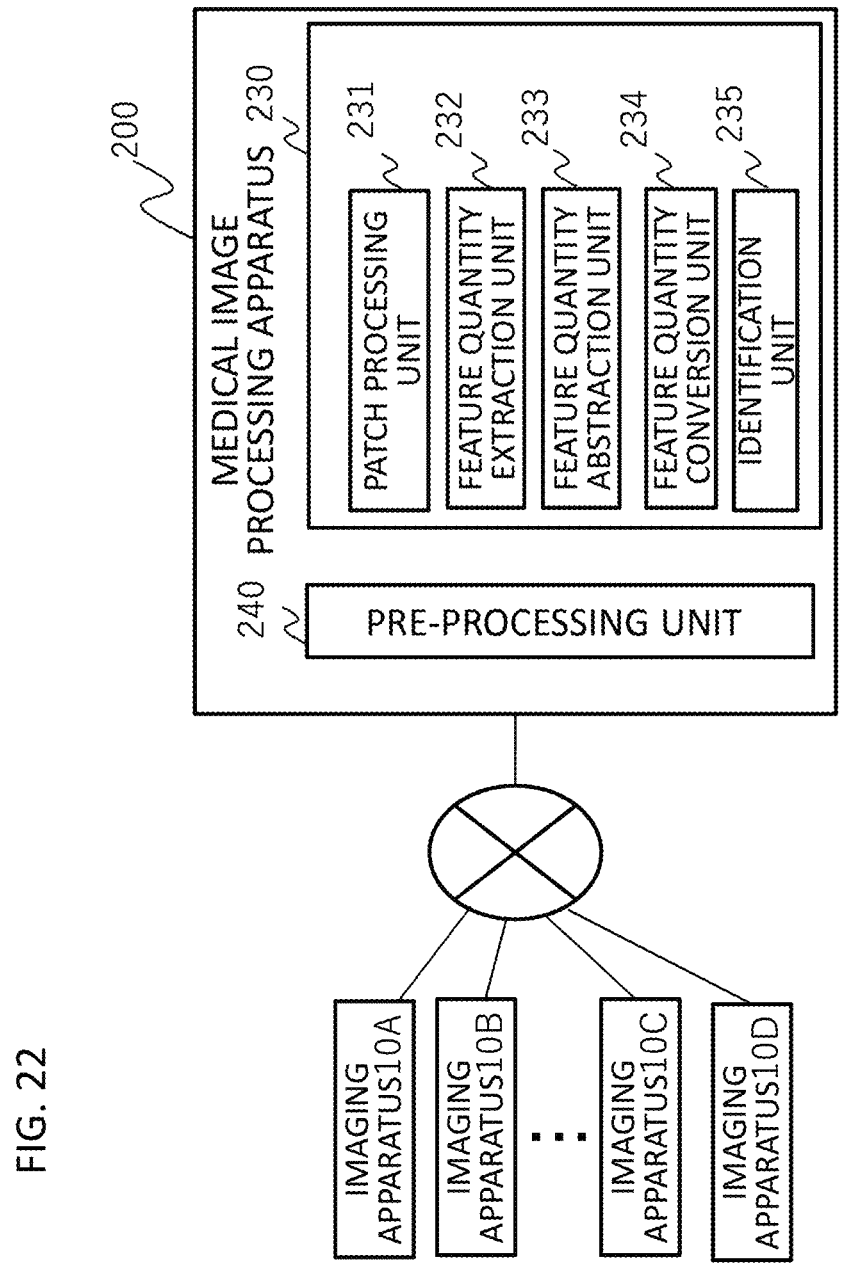
FIG. 22 is a diagram illustrating an overall configuration of an image processing apparatus.

FIG. 1 illustrates the case where the image processing unit 200 including the diagnosis support processing unit 230 is incorporated in the medical imaging apparatus 10. However, some or all of the functions of the image processing unit 200 may be implemented by an image processing apparatus independent of the medical imaging apparatus 10. FIG. 22 illustrates a configuration example of an independent image processing apparatus 20.

The image processing apparatus 20 is a medical image processing apparatus in which the function of the diagnosis support processing unit 230 among the functions of the image processing unit 200 illustrated in FIG. 1 is independent, and is connected to one or a plurality of medical imaging apparatuses 10 (10A, 10B . . . ) via communication or a network. The plurality of medical imaging apparatuses may be imaging apparatuses having different modalities or may be imaging apparatuses installed in different facilities or installation locations. A main function of the image processing apparatus 20 is implemented as software installed in the CPU or GPU, similarly to the image processing unit 200. In addition, although not illustrated in FIG. 22, the input unit 110, the output unit 120, and the storage device 130 illustrated in FIG. 1 are connected to the image processing apparatus 20.

The image processing apparatus 20 receives the image data acquired by each medical imaging apparatus 10, and performs processing by each unit of the diagnosis support processing unit 230 illustrated in FIG. 2. The processing of the image reconstructing unit 210 and the correction processing unit 220 in the image processing unit 200 of FIG. 1 is performed by the image processing unit provided in the medical imaging apparatus 10, in which image reconstruction and correction processing are performed according to the type of medical imaging apparatus. However, the image processing apparatus 20 may have a function of performing image reconstruction and correction processing. Further, the image processing apparatus 20 may include a pre-processing unit 240 that performs pre-processing required to use image data sent from each medical imaging apparatus as an input image of the diagnosis support processing unit 230. The pre-processing is, for example, processing of aligning image sizes and brightness distributions that differ depending on the medical imaging apparatus, processing of removing unnecessary information (for example, background), etc.

The operation of the diagnosis support processing unit 230 of the image processing apparatus 20 is similar to that of each of the above-described embodiments or the modifications thereof. In this operation, the image data sent from the medical imaging apparatus 10 is subjected to processing of extraction and abstraction of the feature quantity and feature quantity conversion, and finally a parameter that serves as a diagnosis support is calculated by processing using the identification model. A processing result of the diagnosis support processing unit 230 may be output to the output unit 120 provided in the image processing apparatus 20, or may be sent to the medical imaging apparatus to which the image data is sent, a facility in which the medical imaging apparatus is placed, a database in another medical institution, etc.

Further, the conversion of the feature quantity in the feature quantity conversion unit 234 is not limited to two captured images, and can be applied to a plurality of different types of captured images. For example, in the case of using images of the imaging apparatuses 10A, 10B, and 10C, a relationship between the feature quantities of the images obtained from the respective imaging apparatuses are mutually learned, and then it is possible to perform mutual conversion from the feature quantity of the image of the imaging apparatus 10A necessary for diagnosis to the feature quantity of the image of the imaging apparatus 10B or the feature quantity of the image of the imaging apparatus 10C, etc. In other words, since it is possible to convert a feature quantity of an image of one imaging apparatus into feature quantities of a plurality of different imaging apparatuses, it is possible to perform highly accurate image diagnosis while suppressing the information collection cost in one examination.

In the first embodiment, a description has been given of an embodiment and a modification thereof that can be applied regardless of the type of imaging unit. An embodiment for each modality will be described below.

Third Embodiment

An embodiment in which the invention is applied to the MRI apparatus will be described.

Figure 23:
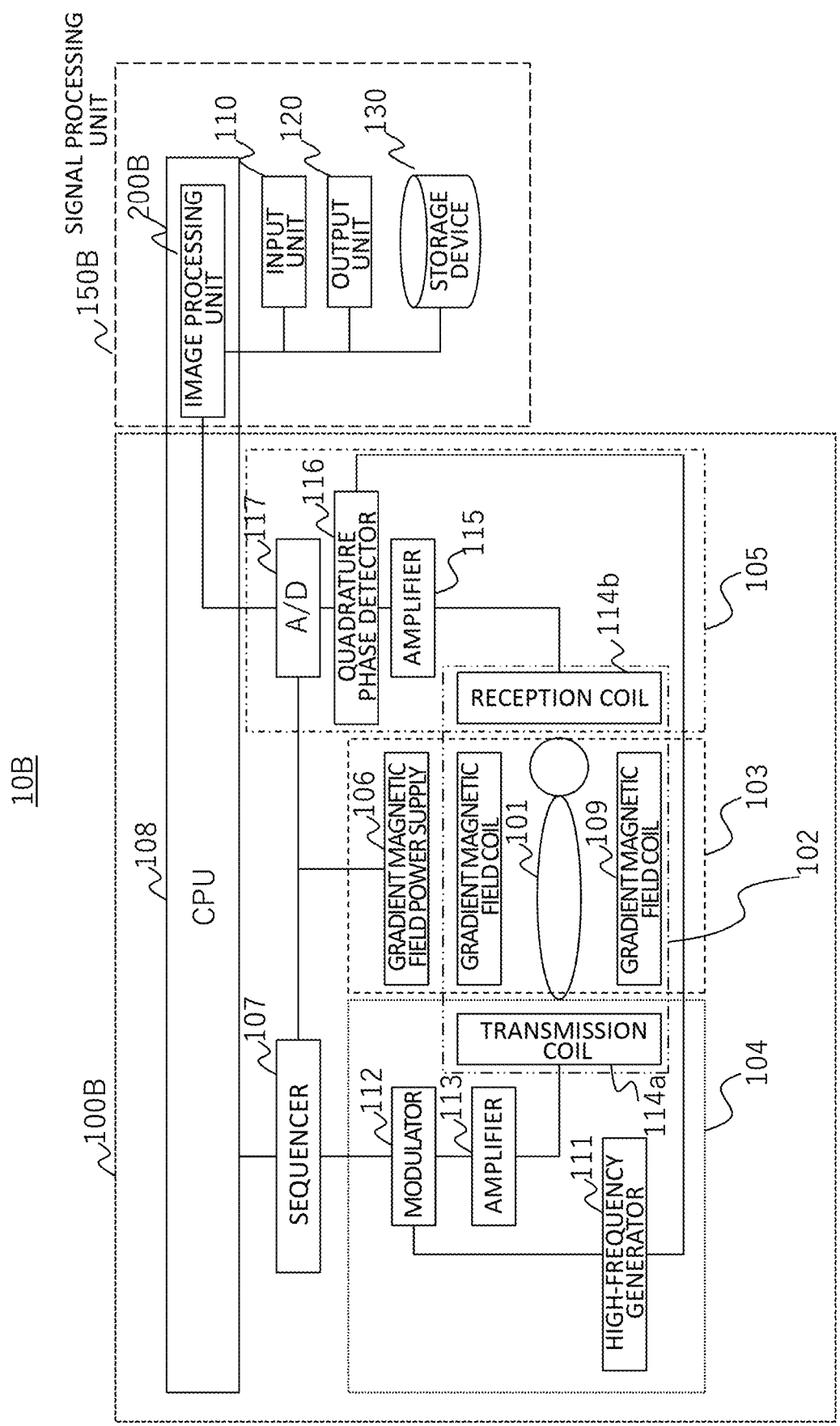
FIG. 23 is a diagram illustrating an overall configuration of a medical imaging apparatus (MRI apparatus) according to a third embodiment.

As illustrated in FIG. 23, an MRI apparatus 10B includes an MR imaging unit 100B corresponding to the imaging unit 100 of the first embodiment, and a signal processing unit 150B that performs calculation such as image reconstruction using a nuclear magnetic resonance signal received from the MR imaging unit 100B.

The MR imaging unit 100B has the same configuration as a conventional MRI apparatus, measures a magnetic resonance signal of an inspection target, and acquires k-space data including the magnetic resonance signal. Specifically, the MR imaging unit 100B includes a static magnetic field generation unit 102 that generates a static magnetic field, a gradient magnetic field generation unit 103 including a gradient magnetic field coil 109 that generates a gradient magnetic field in three axis directions in a static magnetic field space, a transmitter 104 including a transmission coil 114a for applying a high frequency magnetic field to a subject 101 in the static magnetic field space, a receiver 105 including a reception coil 114b for receiving a nuclear magnetic resonance signal generated from the subject 101, and a sequencer 107 for controlling operations of the gradient magnetic field generation unit 103, the transmitter 104, and the receiver 105 according to a predetermined pulse sequence.

The gradient magnetic field generation unit 103 is provided with a gradient magnetic field power supply 106 for driving the gradient magnetic field coil 109, and the transmitter 104 is provided with a high-frequency generator 111 that applies a predetermined high-frequency signal to the transmission coil 114a and irradiates an electromagnetic wave having a nuclear magnetic resonance frequency from the transmission coil 114a, an amplifier 113, a modulator 112, etc. In addition, the receiver 105 includes an amplifier 115 for amplifying a signal detected by the reception coil 114b, a quadrature phase detector 116, an A/D converter 117 for conversion into a digital signal, etc.

The signal processing unit 150B includes an image processing unit 200B that performs a similar process to that of the image processing unit 200 of the first embodiment using a nuclear magnetic resonance signal (k-space data) acquired by the MR imaging unit 100B, an input unit 110 for inputting necessary commands and information to each unit, an output unit 120 for displaying a created image and UI, and a storage device 130 that stores the nuclear magnetic resonance signal acquired by the MR imaging unit 100B, data in a process of calculation, and numerical values such as parameters necessary for calculation.

A function of the signal processing unit 150 is implemented by software installed in the memory and the CPU or GPU. However, a part thereof may be configured by hardware.

A configuration and function of the image processing unit 200B are similar to those of the image processing unit 200 of the first embodiment. Referring to FIG. 1, the image processing unit 200B includes the image reconstructing unit 210, the correction processing unit 220, and the diagnosis support processing unit 230. In addition, as illustrated in FIG. 2, the diagnostic support processing unit 230 includes the patch processing unit 231, the feature quantity extraction unit 232, the feature quantity abstraction unit 233, the feature quantity conversion unit 234, and the identification unit 235.

For the feature quantity extraction unit 232 of the present embodiment, a learned predictive model (FIG. 4: 232M) learned using a combination of an MR image and data of benign or malignant information (such as presence or absence of lesion, benign or malignant, or grade of lesion malignancy) of the image as learning data is used. For the feature quantity abstraction unit 233, a learned predictive model (FIG. 5: 233M) learned using a combination of the feature quantity A extracted by the feature quantity extraction unit 232 and benign or malignant information as learning data is used. For the feature quantity conversion unit 234, for example, a conversion model (FIG. 6: 234M) learned using learning data obtained by combining the feature quantity C extracted from the pathological image to accurately identify the parameter of the pathological image (grade of the tumor part) and the feature quantity B extracted by the feature quantity abstraction unit 233 is used. In addition, for the identification unit 235, an identification model (FIG. 11: 235M) learned using the feature quantity C and the parameter is used.

Upon imaging, the MR imaging unit 100B collects k-space data by an arbitrary imaging method and transmits the k-space data to the image processing unit 200B. The image processing unit 200B performs similar processing to that in the first embodiment. First, the image reconstructing unit 210 generates image data of an MR image in the real space from the k-space data, and the correction processing unit 220 performs correction processing on the generated MR image and inputs the MR image to the diagnosis support processing unit 230. The patch processing unit 231 performs patch processing on the input MR image, and the feature quantity extraction unit 232 extracts the feature quantity A for each patch from image data of the MR image for each patch. The feature quantity abstraction unit 233 converts the feature quantity A into a more abstract feature quantity B. The feature quantity conversion unit 234 further converts this feature quantity B into a feature quantity C extracted from another image (pathological image, etc.), and the identification unit 235 calculates a parameter value from the feature quantity C, integrates the patches into an MR image, and outputs the parameter value and MR image data to the output unit 120.

In the present embodiment, the modification of the first embodiment may be applied to perform the above-described processing of the image processing unit 200B (diagnosis support processing unit 230) only on a desired region (ROI) of the MR image, or cut out the patches by overlapping. Further, by applying the second embodiment, a plurality of MR images acquired by a plurality of imaging methods may be passed to the image processing unit 200B to predict a diagnostic parameter. At this time, additional text information may be input to the diagnosis support processing unit 230.

According to the medical imaging apparatus (MRI apparatus) of the present embodiment, a parameter value used for highly accurate diagnosis can be calculated from an input image (MR image) of a subject, and thus an image showing a highly accurate diagnosis result can be obtained without performing a detailed examination other than the diagnosis using the medical imaging apparatus. In this way, when the MRI apparatus of the present embodiment is used, for example, a diagnosis equivalent to a pathological diagnosis can be performed without performing a pathological examination, and thus it is possible to perform a highly accurate diagnosis while reducing a physical burden on a patient.

Fourth Embodiment

A description will be given of an embodiment in which the invention is applied to the ultrasonic imaging apparatus.

Figure 24:
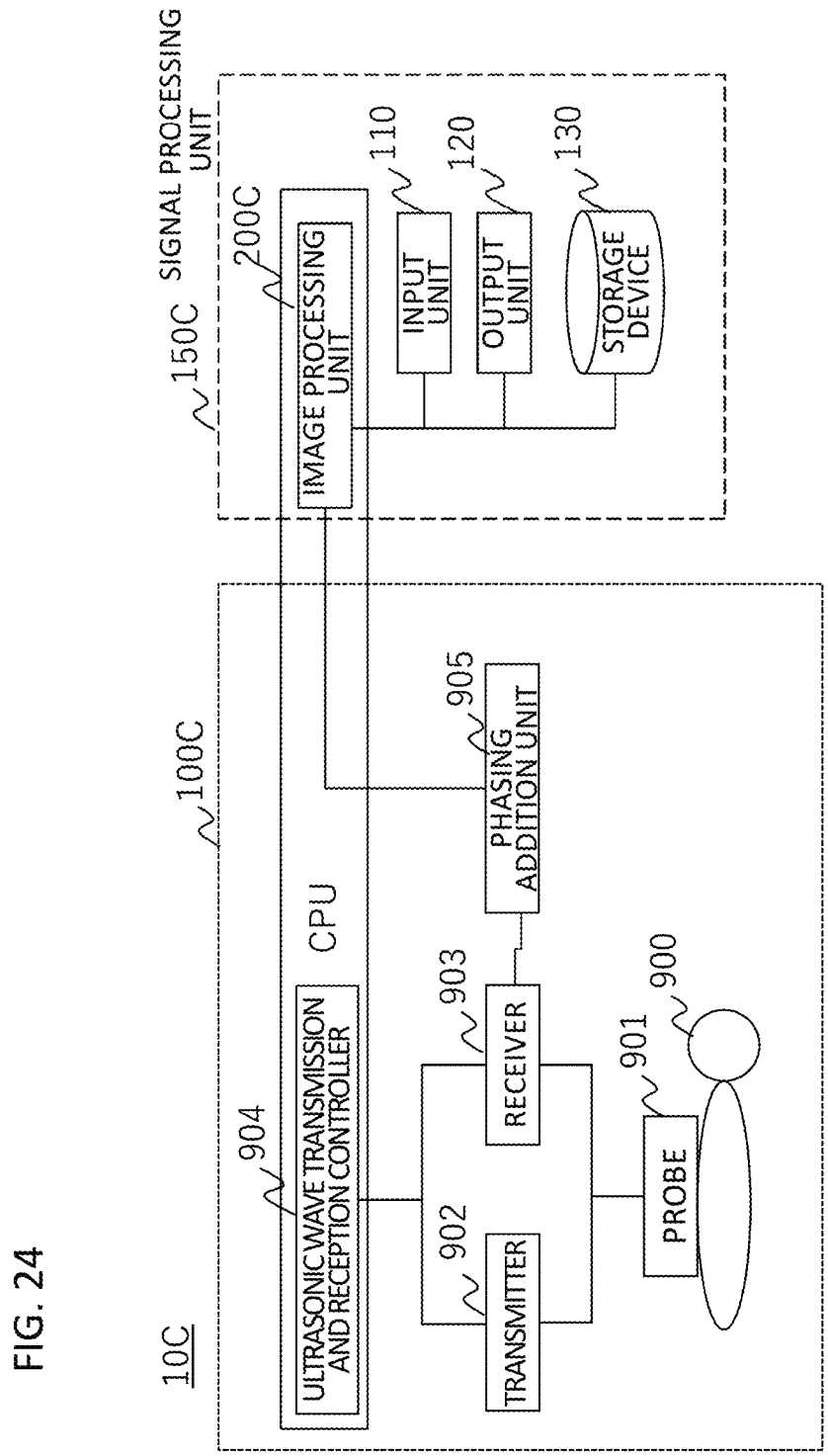
FIG. 24 is a diagram illustrating an overall configuration of a medical imaging apparatus (ultrasonic imaging apparatus) according to a fourth embodiment.

FIG. 24 illustrates an overall outline of an ultrasonic imaging apparatus 10C. This apparatus includes an ultrasonic imaging unit 100C corresponding to the imaging unit 100 of the first embodiment, and a signal processing unit 150C that performs an operation such as image reconstruction using an ultrasonic signal received from the ultrasonic imaging unit 100C.

The ultrasonic imaging unit 100C has a similar configuration to that of a conventional ultrasonic imaging apparatus, and includes an ultrasonic probe 901 that transmits ultrasonic waves to a subject 900, a transmitter 902 that transmits an ultrasonic wave drive signal to the probe 901, an ultrasonic wave receiver 903 that receives an ultrasonic wave signal (RF signal) from the probe 901, a phasing addition unit 905 that performs phasing addition (beamforming) on a signal received by the ultrasonic wave receiver 903, and an ultrasonic wave transmission and reception controller 904 that controls the ultrasonic wave transmitter 902 and the ultrasonic wave receiver 903.

The signal processing unit 150C includes an image processing unit 200C that generates an ultrasonic image from the ultrasonic signal acquired by the imaging unit 100C and performs similar processing to that of the image processing unit 200 of the first embodiment, the input unit 110, the output unit 120, and the storage device 130. The signal processing unit 150C may further include a Doppler processing unit (not illustrated). In the illustrated configuration example, the ultrasonic wave transmission and reception controller 904 and the image processing unit 200C are built in one CPU. However, the ultrasonic wave transmission and reception controller 904 may be built in a CPU different from the image processing unit 200C, or may be a combination of hardware such as a transceiver circuit and control software.

A configuration and function of the image processing unit 200C are similar to those of the image processing unit 200 of the first embodiment, and the diagnosis support processing unit 230 thereof has a similar configuration to that illustrated in FIG. 2. Thus, a repeated description will be omitted.

A model used by the feature quantity extraction unit 232, the feature quantity abstraction unit 233, the feature quantity conversion unit 234, and the identification unit 235 of the present embodiment is similar to that of the third embodiment except that an image input to the diagnosis support processing unit 230 is not an MR image and is an ultrasonic image acquired as follows.

In imaging, ultrasonic waves received by the probe 901 are phased and added in the ultrasonic imaging unit 100C, and an ultrasonic signal is transmitted to the image processing unit 200C. In the image processing unit 200C, the image reconstructing unit 210 first generates an ultrasonic image from the ultrasonic signal, and the correction processing unit 220 corrects the generated ultrasonic image and inputs the ultrasonic image to the diagnosis support processing unit 230. In the diagnosis support processing unit 230, the patch processing unit 210 performs patch processing on the input ultrasonic image, and the feature quantity extraction unit 232 extracts the feature quantity A for each patch from image data of the ultrasonic image. The feature quantity abstraction unit 233 extracts the abstracted feature quantity B obtained by fusing the feature quantity A for each patch. The feature quantity conversion unit 234 converts the feature quantity B into the feature quantity C. The identification unit 235 calculates a parameter value associated with a feature of the pathological image from the feature quantity C, and outputs the parameter value to the output unit 120. The output unit 120 outputs the parameter value and CT image data output from the diagnosis support processing unit 230 in a predetermined display mode.

In the present embodiment, the modification described in the first embodiment and the second embodiment can be applied as appropriate.

According to the ultrasonic imaging apparatus of the present embodiment, since it is possible to calculate a parameter value used for highly accurate diagnosis from an ultrasonic image, it is possible to obtain a highly accurate diagnostic result without performing a detailed examination other than the diagnosis using the ultrasonic imaging apparatus.

Fifth Embodiment

A description will be given of an embodiment in which the invention is applied to the CT apparatus.

Figure 25:
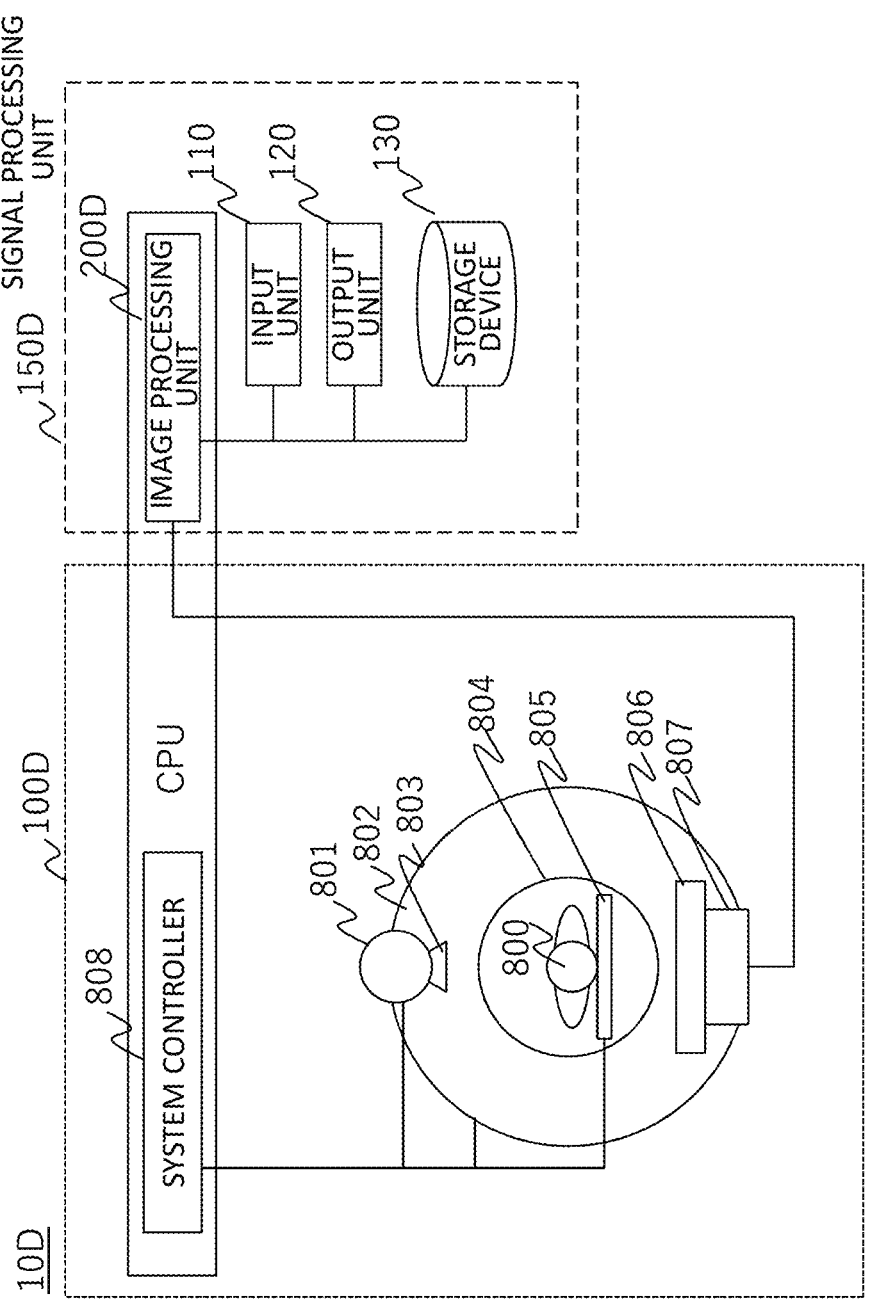
FIG. 25 is a diagram illustrating an overall configuration of a medical imaging apparatus (CT apparatus) according to a fifth embodiment.

FIG. 25 illustrates an overall outline of a CT apparatus 10D. This apparatus is roughly divided into and includes a CT imaging unit 100D corresponding to the imaging unit 100 of the first embodiment, and a signal processing unit 150D that performs an operation such as image reconstruction using a CT image signal received from the CT imaging unit 100D.

The CT imaging unit 100D has a similar configuration to that of a conventional CT apparatus, and includes an X-ray source 801 that irradiates a subject 800 with X-rays, a collimator 803 that limits an X-ray emission range, an X-ray detector 806 that detects transmitted X-rays transmitting the subject 800, a rotating plate 802 having an opening 804 at a center to support the X-ray source 801 and the X-ray detector 806 at opposite positions, a bed 805 for mounting the subject 800 in a space inside the opening 804, a data collection unit 807 that collects an output of the X-ray detector 806 for each piece of projection data, and a system controller 808 that controls an operation of each element included in the CT imaging unit 100D.

The signal processing unit 150D includes an image processing unit 200D that performs similar processing to that of the image processing unit 200 of the first embodiment on a tomographic image (CT image) generated by the imaging unit 100D, the input unit 110, the output unit 120, and the storage device 130. Further, in the illustrated configuration example, the system controller 808 and the image processing unit 200D are built in one CPU. However, the system controller 808 may be built in a CPU different from the image processing unit 200D, or may be a combination of hardware and control software. Similarly, some of functions of the signal processing unit 150D can be configured by hardware.

A configuration and function of the image processing unit 200D are similar to those of the image processing unit 200 of the first embodiment, and the diagnosis support processing unit 230 thereof has a similar configuration to that illustrated in FIG. 2. Thus, a repeated description will be omitted.

A model used by the feature quantity extraction unit 232, the feature quantity abstraction unit 233, the feature quantity conversion unit 234, and the identification unit 235 of the present embodiment is similar to that of the third embodiment except that an image input to the diagnosis support processing unit 230 is not an MR image and is a CT image acquired as follows.

In imaging, the data collection unit 807 collects an X-ray signal of transmitted X-rays detected by the X-ray detector 806 in the CT imaging unit 100D, and transmits the X-ray signal to the image processing unit 200D. In the image processing unit 200D, the image reconstructing unit 210 first generates a CT image, and the correction processing unit 220 corrects the generated CT image and inputs the CT image to the diagnosis support processing unit 230. The patch processing unit 231 performs patch processing on the input CT image, and the feature quantity extraction unit 232 extracts the feature quantity A for each patch from the CT image. The feature quantity abstraction unit 233 integrates the feature quantity A of each patch and converts the feature quantity A into the abstracted feature quantity B. The conversion unit 233 converts the feature quantity B into the feature quantity C that is a feature of the pathological image. The identification unit 235 calculates a parameter value from the feature quantity C, and outputs the parameter value to the output unit 120. The output unit 120 outputs the parameter value and CT image data output from the diagnosis support processing unit 230 in a predetermined display mode.

In the present embodiment, the modification described in the first embodiment and the second embodiment can be applied as appropriate.

According to the CT apparatus of the present embodiment, since it is possible to calculate a parameter value used for highly accurate diagnosis from a CT image, it is possible to obtain a highly accurate diagnostic result without performing a detailed examination other than the diagnosis using the CT apparatus.

What is claimed is:

1. A medical imaging apparatus comprising:
an imager that collects an image signal of an inspection target; and
an image processor that generates first image data from the image signal and performs image processing of the first image data,
wherein the image processor includes
a feature quantity extractor that extracts a first feature quantity from the first image data,
a feature quantity abstractor that uses a plurality of first feature quantities to extract a second feature quantity abstracted from the first feature quantities,
a feature quantity converter that converts the second feature quantity into a third feature quantity extracted by second image data different in type from the first image data,
an identifier that uses the third feature quantity converted by the feature quantity converter to calculate a predetermined parameter value capable of being determined from the second image data,
wherein the feature quantity extractor includes a predictive model learned using the first image data acquired from a plurality of inspection targets,
the feature quantity abstractor includes a predictive model learned by combining the plurality of first feature quantities,
the feature quantity converter includes a feature quantity conversion model learned using a plurality of combinations of the second feature quantity and the third feature quantity,
the identifier includes an identification model learned using a plurality of combinations of the third feature quantity and the parameter value, and
wherein the feature quantity conversion model includes a model learned so that an error of a distance between feature quantities contributing more to identification accuracy in the second feature quantity and the third feature quantity mapped on a predetermined space is reduced by an error back propagation method using a predetermined error function.

2. The medical imaging apparatus according to claim 1, wherein the second image data is image data of a pathological image of the inspection target, and
the third feature quantity includes a feature of the pathological image.

3. The medical imaging apparatus according to claim 1, wherein the image processor includes a patch processing unit that performs patch processing on image data, and
the feature quantity extractor extracts the first feature quantity for each patch of the first image data processed by the patch processing unit.

4. The medical imaging apparatus according to claim 1, wherein the first image includes a plurality of images different in types of imaging apparatuses, imaging conditions, or image types, and the feature quantity extractor extracts the first feature quantity for each of the plurality of images.

5. The medical imaging apparatus according to claim 1, wherein at least one of the first image data and the second image data includes non-image information such as electronic medical record information, various text information, or vital data information.

6. The medical imaging apparatus according to claim 1, wherein the feature quantity conversion model includes two networks of an encoder and a decoder, and when the second feature quantity is input to the encoder, the decoder outputs the third feature quantity.

7. The medical imaging apparatus according to claim 1, wherein the feature quantity conversion model includes a model learned so that an error of a distance between the second feature quantity and the third feature quantity mapped on a predetermined space is reduced by an error back propagation method using a predetermined error function.

8. The medical imaging apparatus according to claim 1, wherein the feature quantity conversion model includes a model learned so that an error between an output of a parameter value calculated by the identifier and teacher data is reduced by an error back propagation method using a predetermined error function.

9. The medical imaging apparatus according to claim 1, wherein the feature quantity conversion model includes a model learned so that an error of a distance between the second feature quantity and the third feature quantity mapped on a predetermined space is reduced and an error between an output of a parameter value calculated by the identifier and teacher data is reduced by an error back propagation method using a predetermined error function.

10. The medical imaging apparatus according to claim 1, further comprising
an output unit that displays an image processed by the image processor,
wherein the output unit displays an image of the first image data and information based on the parameter value in a superimposed or parallel manner.

11. The medical imaging apparatus according to claim 1, further comprising
a region of interest (ROI) setting unit that sets an ROI in image data of the inspection target,
wherein the image processor processes image data in a region set by the ROI setting unit.

12. The medical imaging apparatus according to claim 1, wherein the imager is an MR imager that measures a magnetic resonance signal of an inspection target and acquires k-space data including the magnetic resonance signal, an ultrasonic imager that acquires an ultrasonic signal of an inspection target, or a CT imager that acquires an X-ray signal transmitting an inspection target.

13. The medical imaging apparatus according to claim 1, wherein learned models used by the feature quantity extractor, the feature quantity abstractor, and the feature quantity converter are stored in a cloud connected to the imager via a network.

14. A medical imaging apparatus comprising:
an imager that collects an image signal of an inspection target; and
an image processor that generates first image data from the image signal and performs image processing of the first image data,
wherein the image processor includes
a feature quantity extractor that extracts a first feature quantity from the first image data,
a feature quantity abstractor that uses a plurality of first feature quantities to extract a second feature quantity abstracted from the first feature quantities,
a feature quantity converter that converts the second feature quantity into a third feature quantity extracted by second image data different in type from the first image data,
an identifier that uses the third feature quantity converted by the feature quantity converter to calculate a predetermined parameter value capable of being determined from the second image data,
wherein the feature quantity extractor includes a predictive model learned using the first image data acquired from a plurality of inspection targets,
the feature quantity abstractor includes a predictive model learned by combining the plurality of first feature quantities,
the feature quantity converter includes a feature quantity conversion model learned using a plurality of combinations of the second feature quantity and the third feature quantity,
the identifier includes an identification model learned using a plurality of combinations of the third feature quantity and the parameter value, and
wherein the feature quantity conversion model includes a model learned so that an error of a distance between feature quantities contributing more to identification accuracy in the second feature quantity and the third feature quantity mapped on a predetermined space is reduced and an error between an output of a parameter value calculated by the identifier and teacher data is reduced by an error back propagation method using a predetermined error function.

* * * * *